US010378050B2

(12) United States Patent
Wang et al.

(10) Patent No.: US 10,378,050 B2
(45) Date of Patent: Aug. 13, 2019

(54) POLYMERIZATION OF NUCLEIC ACIDS USING PROTEINS HAVING LOW ISOELECTRIC POINTS

(71) Applicant: LIFE TECHNOLOGIES CORPORATION, Carlsbad, CA (US)

(72) Inventors: Jonathan Wang, Mountain View, CA (US); David Dupont, Redwood City, CA (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 15/397,938

(22) Filed: Jan. 4, 2017

(65) Prior Publication Data

US 2017/0114391 A1 Apr. 27, 2017

Related U.S. Application Data

(62) Division of application No. 14/124,667, filed as application No. PCT/US2012/041687 on Jun. 8, 2012, now Pat. No. 9,567,628.

(60) Provisional application No. 61/494,797, filed on Jun. 8, 2011.

(51) Int. Cl.
*C12Q 1/68* (2018.01)
*C12Q 1/686* (2018.01)
*C12Q 1/6844* (2018.01)
*C12N 9/12* (2006.01)

(52) U.S. Cl.
CPC ............ *C12Q 1/686* (2013.01); *C12N 9/1252* (2013.01); *C12Q 1/6846* (2013.01); *C12Y 207/07007* (2013.01)

(58) Field of Classification Search
CPC ...................................................... C12Q 1/686
USPC ................................................ 435/6.1, 6.12
See application file for complete search history.

(56) References Cited

U.S. PATENT DOCUMENTS

| 5,210,036 | A | 5/1993 | Comb et al. |
| 5,726,021 | A | 3/1998 | Britschgi et al. |
| 5,730,990 | A | 3/1998 | Greenwald et al. |
| 5,766,890 | A | 6/1998 | Kacian et al. |
| 5,814,502 | A | 9/1998 | Hoeltke et al. |
| 5,846,701 | A | 12/1998 | Kacian et al. |
| 5,871,975 | A | 2/1999 | Kacian et al. |
| 5,876,992 | A | 3/1999 | De Rosier et al. |
| 6,127,155 | A | 10/2000 | Gelfand et al. |
| 6,150,094 | A | 11/2000 | Maier et al. |
| 6,242,235 | B1 | 6/2001 | Shultz et al. |
| 6,617,136 | B2 | 9/2003 | Parthasarathy et al. |
| 6,740,510 | B2 | 5/2004 | Kautzer et al. |
| 6,767,723 | B2 | 7/2004 | Tonoike |
| 7,094,539 | B2 | 8/2006 | Gu et al. |
| 7,422,882 | B2 | 9/2008 | Kuroita et al. |
| 7,425,423 | B1 | 9/2008 | Ankenbauer et al. |
| 7,638,276 | B2 | 12/2009 | Griffiths et al. |
| 7,803,929 | B2 | 9/2010 | Melkonyan et al. |
| 7,846,703 | B2 | 12/2010 | Kobayashi et al. |
| 7,972,828 | B2 | 7/2011 | Ward et al. |
| 7,973,154 | B2 | 7/2011 | Melkonyan et al. |
| 8,012,685 | B2 | 9/2011 | Shannon et al. |
| 8,173,401 | B2 | 5/2012 | Chang et al. |
| 8,192,960 | B2 | 6/2012 | Peters et al. |
| 8,202,972 | B2 | 6/2012 | Nelson et al. |
| 8,404,464 | B2 | 3/2013 | Ward et al. |
| 8,460,934 | B2 | 6/2013 | Chang et al. |
| 8,980,333 | B2 | 3/2015 | Angrish et al. |
| 9,493,414 | B2 | 11/2016 | Angrish et al. |
| 9,567,628 | B2* | 2/2017 | Wang .................. C12Q 1/6846 |
| 2002/0127587 | A1 | 9/2002 | Simms et al. |
| 2002/0168658 | A1 | 11/2002 | Weissman et al. |
| 2003/0017567 | A1 | 1/2003 | Parthasarathy et al. |
| 2003/0022231 | A1 | 1/2003 | Wangh et al. |
| 2003/0108919 | A1 | 6/2003 | Kautzer et al. |
| 2005/0037392 | A1 | 2/2005 | Griffiths et al. |
| 2005/0277121 | A1 | 12/2005 | Pasloske et al. |
| 2006/0068390 | A1 | 3/2006 | Tillett et al. |
| 2006/0160122 | A1 | 7/2006 | Harrold et al. |
| 2006/0234228 | A1 | 10/2006 | Oshima et al. |
| 2006/0292578 | A1 | 12/2006 | Zheng et al. |
| 2008/0003574 | A1 | 1/2008 | Michalik et al. |
| 2008/0003575 | A1 | 1/2008 | Michalik et al. |
| 2008/0064071 | A1 | 3/2008 | Hogrefe et al. |
| 2008/0145910 | A1* | 6/2008 | Ward .................. C12Q 1/6848 435/188 |
| 2008/0166772 | A1 | 7/2008 | Hollinger et al. |
| 2008/0199857 | A1 | 8/2008 | Lee |
| 2009/0111149 | A1 | 4/2009 | Cao |
| 2009/0155777 | A1 | 6/2009 | Yang et al. |

(Continued)

FOREIGN PATENT DOCUMENTS

CN 101617045 A 12/2009
EP 0455744 B1 8/1993

(Continued)

OTHER PUBLICATIONS

Mei-Yun (Applied Microbiology and Biotechnology, vol. 77, 2007, pp. 645-656).* Mopett et al. (Leukemia, 2003, pp. 268-270).*
Al-Soud, et al., "Effects of amplification facilitators on diagnostic PCR in the presence of blood, feces, and meat", Journal of Clinical Microbiology, Dec. 2000, 4463-4470.
Fu, X., et al., "Waste recombinant DNA: Effectiveness of thermo-treatment to manage potential gene pollution", Environmental Pollution, Aug. 1, 2009, 2536-2541.
Hunter, S., et al., "The QPCR assay for analysis of mitochondrial DNA damage, repair, and relative copy number", Methods: A Companion to Methods in Enzymology, 1 Aug. 2010, 444-451.
Kreader, Carol A., et al., "Relief of Amplification Inhibition in PCR with Bovine Serum Albumin or T4 Gene 32 Protein", Applied and Environmental Microbiology, Mar. 1996, 1102-1106.

(Continued)

*Primary Examiner* — Jezia Riley

(57) ABSTRACT

This disclosure relates to the use of one or more proteins (e.g., globular proteins) having a low isoelectric point and/or a limited number (e.g., zero) of modifying groups in nucleic acid polymerization and/or amplification reactions such as polymerase chain reaction (PCR).

14 Claims, 28 Drawing Sheets

(56) References Cited

U.S. PATENT DOCUMENTS

| | | |
|---|---|---|
| 2009/0325236 A1 | 12/2009 | Griffiths et al. |
| 2010/0035238 A1 | 2/2010 | Westberry et al. |
| 2010/0099150 A1 | 4/2010 | Fang et al. |
| 2010/0159528 A1 | 6/2010 | Liu et al. |
| 2011/0015379 A1 | 1/2011 | Mori et al. |
| 2011/0046205 A1 | 2/2011 | Kosak et al. |
| 2011/0171717 A1 | 7/2011 | Kobayashi et al. |
| 2011/0236891 A1 | 9/2011 | Li et al. |
| 2011/0287436 A1 | 11/2011 | Shannon et al. |
| 2012/0202700 A1 | 8/2012 | Pierson et al. |
| 2012/0302449 A1 | 11/2012 | Dong et al. |
| 2012/0322066 A1 | 12/2012 | Angrish et al. |
| 2013/0066062 A1 | 3/2013 | Sano et al. |
| 2013/0084574 A1 | 4/2013 | Dong et al. |
| 2015/0184145 A1 | 7/2015 | Angrish et al. |

FOREIGN PATENT DOCUMENTS

| | | |
|---|---|---|
| EP | 0258017 B1 | 6/1997 |
| EP | 0455430 B1 | 7/1998 |
| EP | 0506825 B1 | 8/1998 |
| EP | 0550687 B1 | 6/1999 |
| EP | 0550696 B1 | 11/2000 |
| EP | 0624641 B1 | 12/2000 |
| EP | 0632134 B1 | 9/2001 |
| EP | 0671473 B1 | 10/2001 |
| EP | 0544789 B1 | 3/2003 |
| EP | 0892058 B1 | 5/2006 |
| EP | 0931151 B1 | 11/2006 |
| EP | 1390545 B1 | 11/2006 |
| EP | 1507002 B1 | 12/2006 |
| EP | 1050587 B1 | 4/2007 |
| EP | 1088060 B1 | 5/2007 |
| EP | 1522582 B1 | 7/2007 |
| EP | 1458744 B1 | 8/2007 |
| EP | 1482036 B1 | 10/2007 |
| EP | 0776970 B1 | 4/2008 |
| EP | 1505151 B1 | 5/2008 |
| EP | 1718743 B1 | 8/2009 |
| EP | 1154017 B1 | 1/2010 |
| EP | 1772523 B1 | 1/2010 |
| EP | 2175020 A1 | 4/2010 |
| EP | 1904518 B1 | 10/2010 |
| EP | 1842922 B1 | 5/2011 |
| EP | 2333102 A1 | 6/2011 |
| EP | 1540009 B1 | 9/2011 |
| EP | 1905828 B1 | 8/2012 |
| EP | 0894860 B1 | 12/2012 |
| EP | 1908832 B1 | 12/2012 |
| EP | 2314596 B1 | 6/2013 |
| EP | 2115131 B1 | 7/2013 |
| GB | 1087415 | 10/1967 |
| JP | 60-089458 A | 5/1985 |
| JP | H05178731 A | 7/1993 |
| JP | H061712 A | 1/1994 |
| JP | H061715 A | 1/1994 |
| RO | 83776 | 3/1984 |
| WO | 1998/044161 A1 | 10/1998 |
| WO | WO 98/44161 | * 10/1998 |
| WO | 2008/013885 A2 | 1/2008 |
| WO | 2008/033936 A2 | 3/2008 |
| WO | 2008/144556 A1 | 11/2008 |
| WO | WO 2008/144556 | * 11/2008 |
| WO | 2010/002938 A2 | 1/2010 |
| WO | WO 2010/002938 | * 1/2010 |
| WO | WO-2011046972 A2 | 4/2011 |
| WO | 2011/163120 A1 | 12/2011 |
| WO | 2012/170907 A2 | 12/2012 |
| WO | 2012/170908 A1 | 12/2012 |
| WO | 2013/050881 A2 | 4/2013 |

OTHER PUBLICATIONS

Moppett, J., et al., "Inhibition affecting RQ-PCR-based assessment of minimal residual disease in acute lymphoblastic leukemia: reversal by addition of bovine serum albumin", Leukemia, Jan. 1, 2003, 268-270.

Nagai, et al., "Additive Effects of Bovine Serum Albumin, Dithiothreitol, and Glycerol on PCR", Biochemistry and Molecular Biology International, Jan. 1, 1998, 157-163.

Nakamura, et al., English Abstract JP6001712, Chemical Abstracts Service, Jan. 11, 1994, 3 pages.

Nakamura, et al., English Abstract JP6001715, Chemical Abstracts Service, Jan. 11, 1994, 2 pages.

Nakamura, et al., English Abstract JP60089458, Chemical Abstracts Service, May 20, 1985, 4 pages.

Nakamura, et al., English Abstract JP6049440, Chemical Abstracts Service, Feb. 22, 1994, 1 page.

PCT/US2012/041687, International Search Report and Written Opinion dated Jan. 11, 2013, 25 pages.

PCT/US2012/041688, Notification of Transmittal of the International Search Report and the Written Opinion of the International Searching Authority, or the Declaration, dated Oct. 19, 2012, 14 pages.

PCT/US2014/062222, International Search Report and Written Opinion dated Dec. 22, 2014, 9 pages.

STN Abstract: Nakamura, et al., JP Pat. No. 4060102 B issued Sep. 25, 1992.

Wang, Mei-Yun, et al., "Improving PCR and qPCR detection of hydrogenase A (hydA) associated with Clostridia in purge cultures and environmental sludges using bovine serum albumin", Applied Microbiology and Biotechnology, Oct. 2, 2007, 645-656.

Wang, Xiangcheng, et al., "An Improved Method of Synthesis of 5-Deoxy-D-ribose", Chemical World, vol. 4, 2008, 226-228.

Extended European Search Report for Application No. 18185275.7, dated Mar. 1, 2019, 8 pages.

* cited by examiner

POLYMERIZATION OF NUCLEIC ACIDS USING PROTEINS HAVING LOW ISOELECTRIC POINTS

CROSS-REFERENCE TO RELATED APPLICATIONS

This application is a Divisional of U.S. patent application Ser. No. 14/124,667, filed Jan. 8, 2014 which is a U.S. National Application filed under 35 U.S.C. § 371 of International Application No. PCT/US2012/041687, filed Jun. 8, 2012, which claims the benefit of priority under 35 U.S.C. § 119(e) to U.S. Provisional Patent Application No. 61/494,797, filed Jun. 8, 2011, the disclosure of which is incorporated herein by reference in its entirety.

FIELD

This disclosure relates to the use of one or more proteins (e.g., globular proteins) having a low isoelectric point and/or a limited number (e.g., zero) of modifying groups in nucleic acid polymerization and/or amplification reactions such as polymerase chain reaction (PCR).

BACKGROUND

Many widely known recombinant nucleic acid (e.g., DNA, RNA) techniques involve polymerizing and/or amplifying DNA. One such example is the polymerase chain reaction (PCR). During PCR, the reaction cycles repeatedly between at least two temperatures, a low and a high temperature (e.g., 55° C. and 95° C.) in the presence of a thermostable DNA polymerase enzyme. The total period of time spent at the high temperature over the course of the reaction depends upon the total number of cycles, the duration of the high temperature step of each cycle, and the ramp speed (i.e., the rate at which the thermocycler changes from one temperature to another). Although the DNA polymerases used in PCR are highly thermostable, they tend to become inactive at high temperatures over time. Furthermore, these polymerases may also become inactive by being introduced into reaction mixture environments with sub-optimal concentrations of cofactors, or that have sub-optimal pH levels, or that include the presence of chemical or biological inhibitors.

One way of stabilizing an enzyme under such conditions is to add a stabilizing agent, such as a surfactant. Surfactants, such as detergents, are surface-active compounds that stabilize the interface between the active form of an enzyme and its liquid environment. For example, the activity of Taq DNA polymerase has been stabilized by the addition of nonionic detergents, such as NP-40 or Tween® 20 (Bachmann, et al. *Nuc. Acids Res.* 18(5): 1309 (1990)). In some applications, however, detergent-stabilized (e.g., Tween® 20) DNA polymerases have low efficiencies of amplification or lead to the amplification of non-specific products. There is a need, therefore, for reagents and methods that improve the efficiency and/or stability of thermostable DNA polymerases in solution during polymerization and/or amplification reactions.

BRIEF DESCRIPTION OF THE DRAWINGS

All amplification plots shown herein graphically represent target nucleic acid amplification as ΔRn (y-axis) as a function of cycle number (x-axis).

SUMMARY

Figure 1:
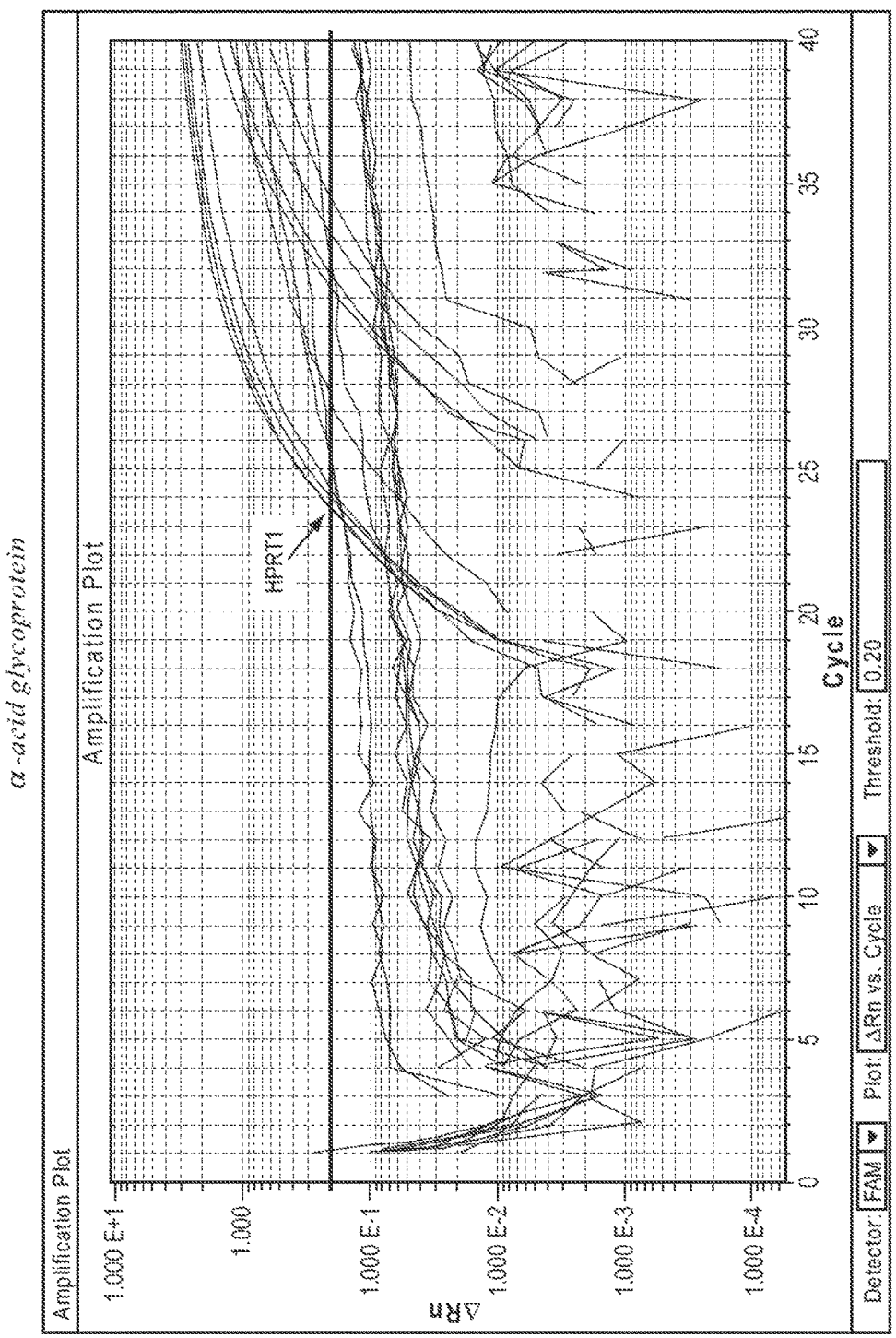
FIG. 1. An amplification plot of an amplification reaction using α-acid glycoprotein with hypoxanthine phosphoriboxyltransferase (HPRT1) as a target nucleic acid according to certain exemplary embodiments of the methods and compositions disclosed herein.
Figure 2:
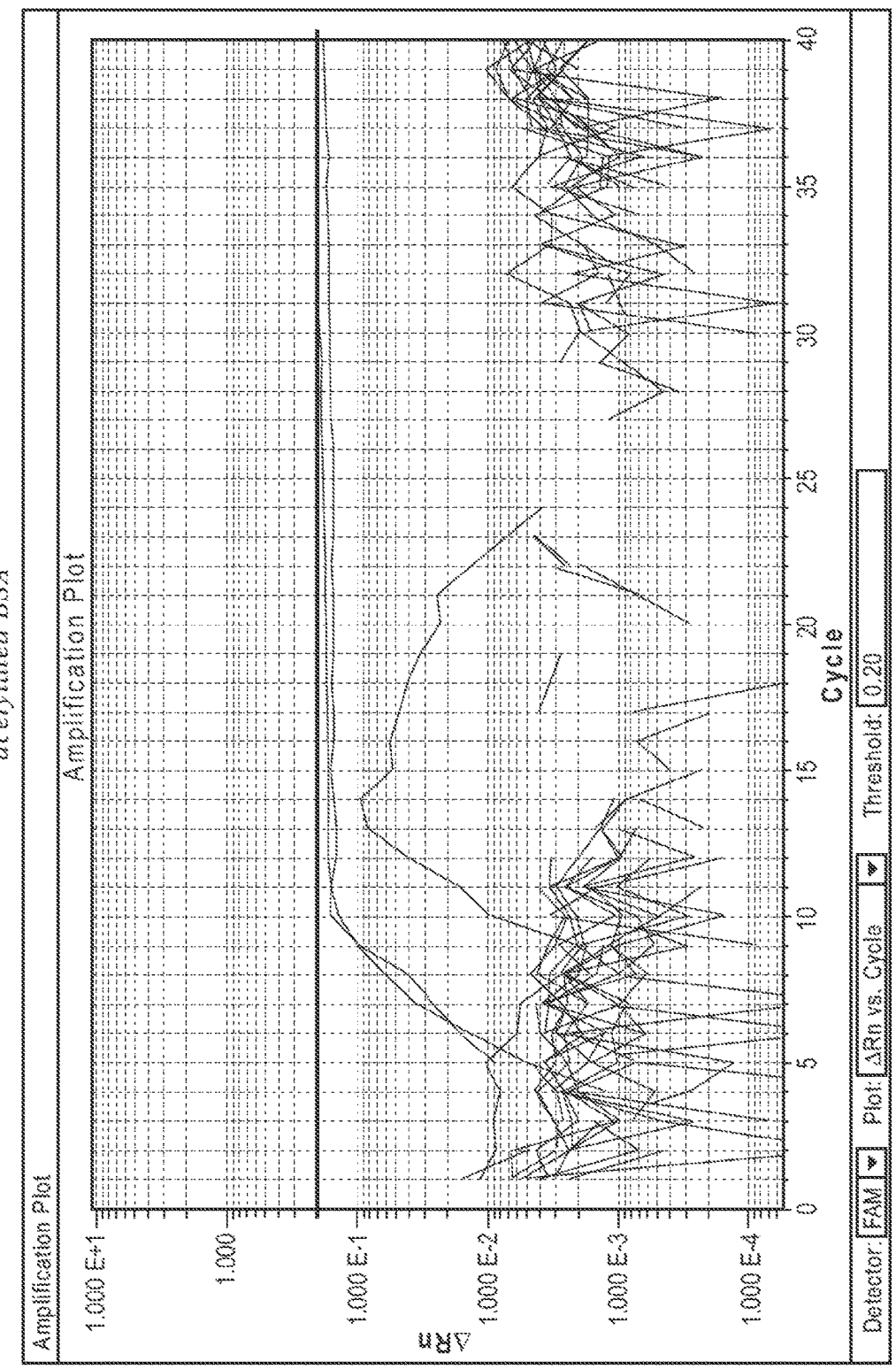
FIG. 2. An amplification plot of an amplification reaction using acetylated bovine serum albumin (acetylated BSA) according to certain exemplary embodiments of the methods and compositions disclosed herein.
Figure 3:
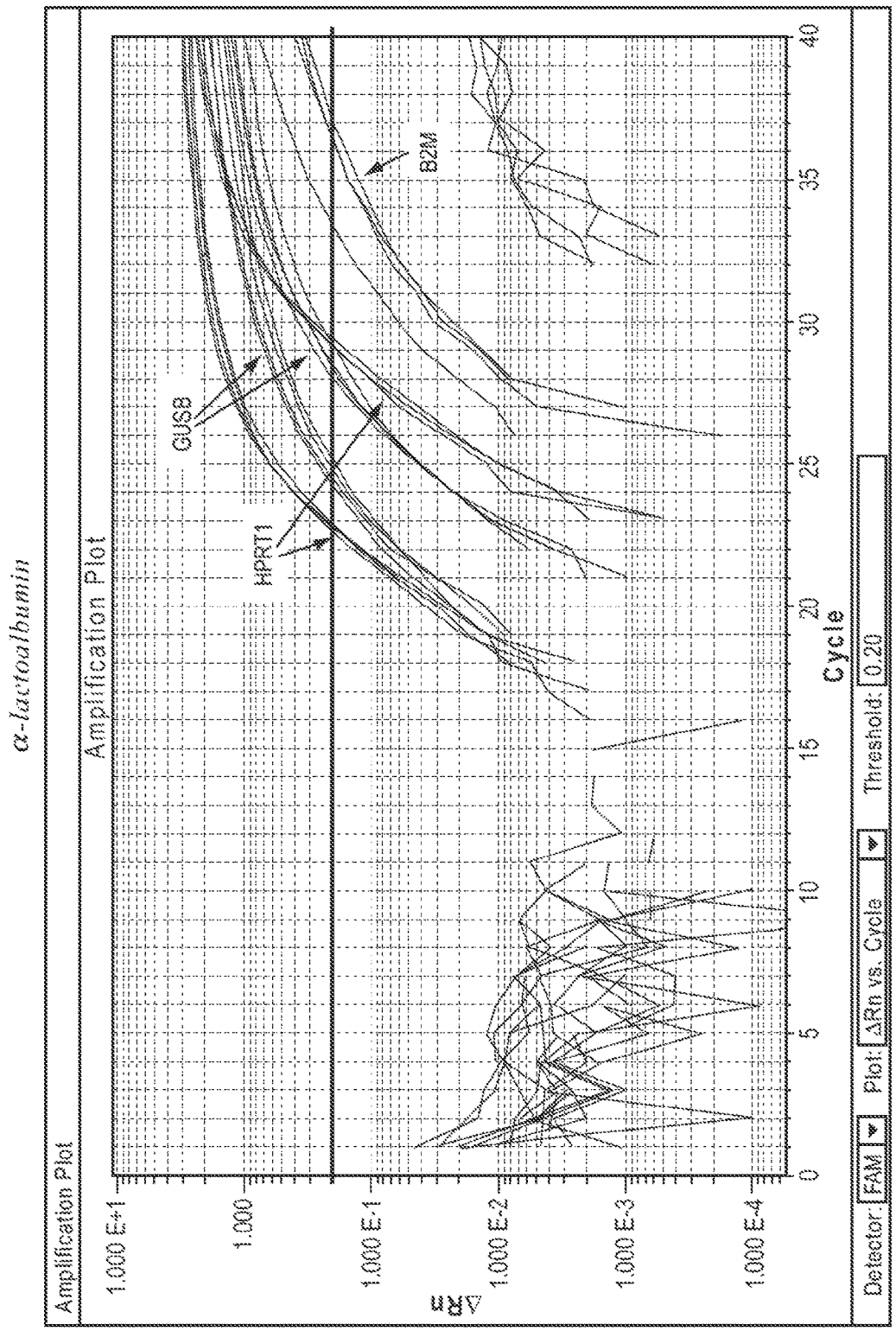
FIG. 3. An amplification plot of an amplification reaction using α-lactoalbumin with HPRT1, glucuronidase beta (GUSB) or beta-2 microglobulin (B2M) as target nucleic acids according to certain exemplary embodiments of the methods and compositions disclosed herein.
Figure 4:
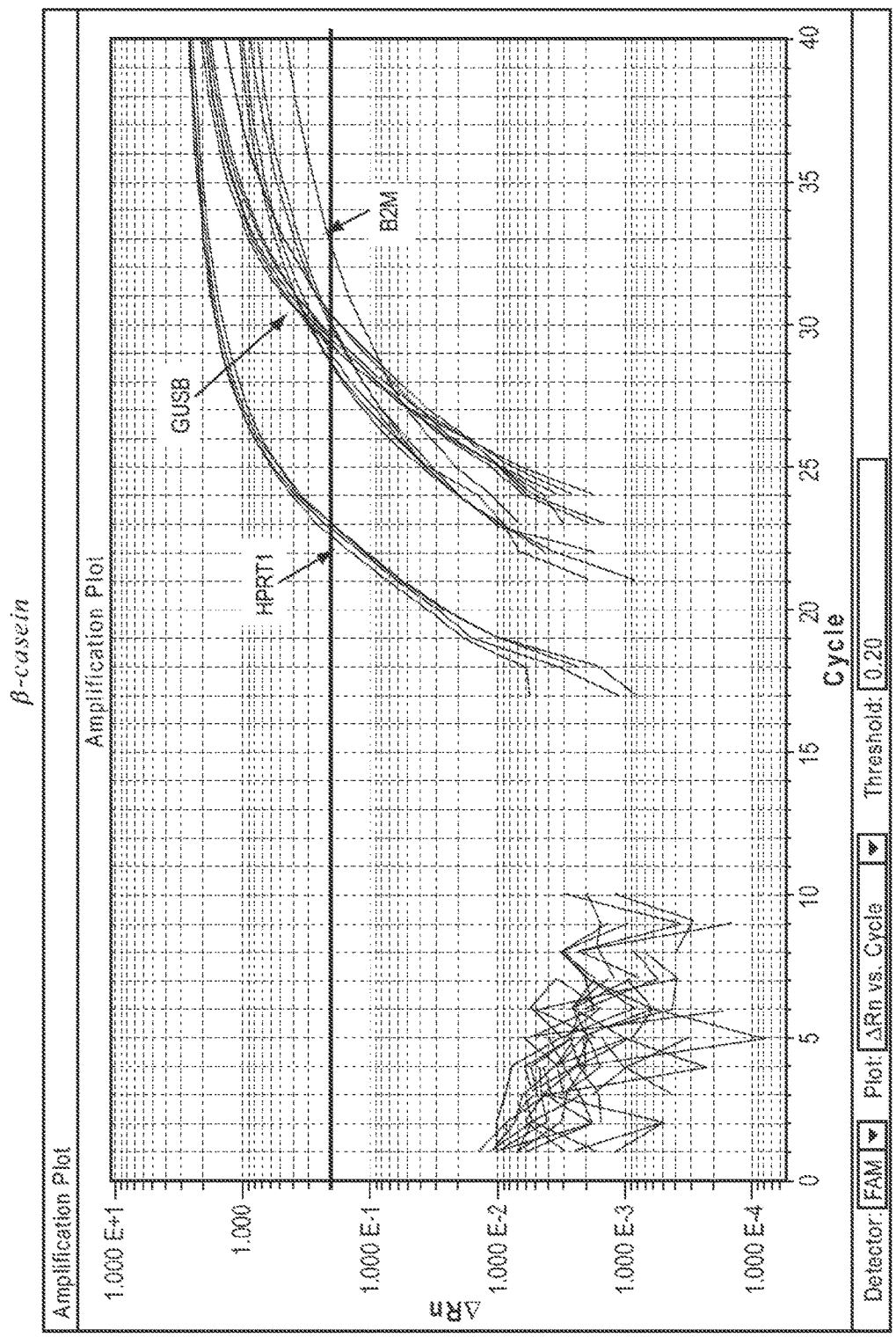
FIG. 4. An amplification plot of an amplification reaction using β-casein with HPRT1, GUSB or B2M as target nucleic acids according to certain exemplary embodiments of the methods and compositions disclosed herein.

Provided herein are methods for polymerizing and/or amplifying a nucleic acid molecule comprising mixing a target nucleic acid with at least one polymerase, at least one primer, dNTPs, and at least one protein having a low isoelectric point, and polymerizing and/or amplifying the target nucleic acid. In certain embodiments, the methods for polymerizing and/or amplifying a nucleic acid molecule comprise mixing a target nucleic acid with at least one polymerase, at least one primer, dNTPs, at least one protein having a low isoelectric point, and optionally at least one detergent, and polymerizing and/or amplifying the target nucleic acid. In certain embodiments, the protein having a low isoelectric point may be globular and/or comprise limited (e.g., none) modifying groups. In certain embodiments, the protein having a low isoelectric point may be globular and have no modifying groups. In certain embodiments, the protein having a low isoelectric point is different than the polymerase.

In certain embodiments, a nucleic acid polymerization and/or amplification reaction mixture comprising at least one polymerase and at least one protein having a low isoelectric point is provided. In certain embodiments, a nucleic acid polymerization and/or amplification reaction mixture comprising at least one polymerase, at least one protein having a low isoelectric point, and optionally at least one detergent, is provided. In certain embodiments, the reaction mixture may further comprise dNTPs and/or at least one primer. In certain embodiments, a nucleic acid polymerase and/or amplification reaction mixture comprises at least one protein having a low isoelectric point, at least one polymerase, and is substantially free of detergent.

In certain embodiments, the methods and the reaction mixture may further comprise a detectable label (e.g., as part of the primer and/or on a probe). The methods may also include one or more steps for detecting and/or quantitating the detectable label in order to detect and/or quantitate the polymerized and/or amplified nucleic acid. In certain embodiments, methods and reaction mixtures for inhibiting inactivation of a polymerase during a polymerization and/or amplification reaction (e.g., thermal cycling process) include at least one protein having a low isoelectric point in the reaction mixture. In certain embodiments, methods and reaction mixtures for inhibiting inactivation of a polymerase during a polymerization and/or amplification reaction (e.g., thermal cycling process) include at least one protein having a low isoelectric point and optionally at least one detergent in the reaction mixture. In certain embodiments, the at least one protein having a low isoelectric point may substitute for a detergent in a polymerization and/or amplification reaction. In certain embodiments, the reaction mixture includes at least one protein having a low isoelectric point and is substantially free of detergent. In certain embodiments, methods and reaction mixtures are provided such that polymerization and/or amplification of a target nucleic acid occurs in the presence of at least one protein having a low isoelectric point, and wherein the polymerization and/or amplification of the target nucleic acid does not substantially occur in the absence of the at least one protein having a low isoelectric point.

In certain embodiments, methods for providing an enzyme having polymerase activity and at least one protein having a low isoelectric point, and combining the same to form a reaction mixture that stabilizes the polymerase activity of the enzyme are described herein. In some embodiments, the methods include providing an enzyme having polymerase activity and at least one protein having a low isoelectric point, and optionally at least one detergent, and combining the same to form a reaction mixture that stabilizes the polymerase activity of the enzyme. In some embodiments, the methods include providing an enzyme having polymerase activity and at least one protein having a low isoelectric point, and combining the same to form a reaction mixture that is free of detergent and that stabilizes the polymerase activity of the enzyme. In certain embodiments, the methods described herein provide stabilization of the polymerase activity with at least one protein having a low isoelectric point such that the stabilized polymerase has an activity that is similar to (e.g., approximately the same) or greater than activity when stabilized by a detergent, such as NP-40, Tween® 20, and/or a detergent of Formula I.

In certain embodiments, the at least one protein having a low isoelectric point, or at least one protein having a low isoelectric point and optionally at least one detergent, or at least one protein having a low isoelectric point and is free of detergent, wherein the reaction mixture reduces the inhibition of the activity of a polymerase therein by, for example, other components of the reaction mixture. In certain embodiments, the polymerase is thermostable. In certain embodiments, the methods described herein provide increased amplification and/or polymerization efficiency with at least one protein having a low isoelectric point such that the amplification and/or polymerization efficiency is similar to (e.g., approximately the same) or greater than the amplification and/or polymerization efficiency with a detergent such as, for example, NP-40, Tween® 20, and/or a detergent of Formula I. The amplification and/or polymerization efficiency may be determined by various methods known in the art, including, but not limited to, determination of calibration dilution curves and slope calculation, determination using qBase software as described in Hellemans et al., *Genome Biology* 8:R19 (2007), determination using the delta delta Cq (ΔΔCq) calculation as described by Livak and Schmittgen, *Methods* 25:402 (2001), or by the method as described by Pfaffl, *Nucl. Acids Res.* 29:e45 (2001), all of which are herein incorporated by reference in their entirety. In some embodiments, the at least one protein having a low isoelectric point described herein may substitute for a detergent in an amplification reaction. In certain embodiments, the reaction mixture includes at least one protein having a low isoelectric point and is substantially free of detergent. In certain embodiments, methods and reaction mixtures are provided such that polymerization and/or amplification of the target nucleic acid occurs in the presence of at least one protein having a low isoelectric point, and wherein the polymerization and/or amplification of the target nucleic acid does not substantially occur in the absence of the at least one protein having a low isoelectric point.

In certain embodiments, compositions comprising a polymerase and, for example, at least one protein having a low isoelectric point are also provided herein. In certain embodiments, compositions comprising a polymerase and, for example, at least one protein having a low isoelectric point, and optionally at least one detergent, are provided herein. In certain embodiments, compositions comprising a polymerase and, for example, at least one protein having a low isoelectric point, wherein the composition is substantially free of detergent are provided herein. Kits comprising reagents and the like necessary to carry out such methods or prepare such mixtures are also provided.

DETAILED DESCRIPTION

Described herein are methods for polymerizing and/or amplifying a nucleic acid molecule comprising mixing a target nucleic acid with at least one polymerase and at least one protein having a low isoelectric point and polymerizing and/or amplifying the target nucleic acid. In certain embodiments, the methods for polymerizing and/or amplifying a nucleic acid molecule comprise mixing a target nucleic acid with at least one polymerase and at least one protein having a low isoelectric point, and optionally at least one detergent, and polymerizing and/or amplifying the target nucleic acid. In certain embodiments, the protein having a low isoelectric point may be globular and/or comprise limited (e.g., none) modifying groups. In certain embodiments, the protein having a low isoelectric point may be globular and have no modifying groups. In certain embodiments, the protein having a low isoelectric point is different than the polymerase.

In certain embodiments, polymerization and/or amplification a nucleic acid reaction mixture comprising at least one polymerase and at least one protein having a low isoelectric point is provided. In certain embodiments, a nucleic acid polymerization and/or amplification reaction mixture comprising at least one polymerase, at least one protein having a low isoelectric point, and optionally at least one detergent is provided. In certain embodiments, the reaction mixture may further comprise dNTPs and/or at least one primer. In certain embodiments, a nucleic acid polymerization and/or amplification reaction mixture comprising at least one polymerase and at least one protein having a low isoelectric point is substantially free of detergent. In certain embodiments, the methods and the reaction mixture may further comprise a detectable label (e.g., as part of the primer and/or on a probe). The methods may also include one or more steps for detecting and/or quantitating the detectable label in order to detect and/or quantitate the polymerized and/or amplified nucleic acid.

Exemplary polymerization and/or amplification reactions may include, for example, polymerase chain reaction (PCR) and the like (e.g., as described herein). In some embodiments, the presence of the at least one protein having a low isoelectric point may stabilize the polymerase within a reaction mixture, decrease inhibition of the polymerase within a reaction mixture, and/or increase the polymerization and/or amplification efficiency of the polymerase in the reaction mixture. As such, methods and reaction mixtures comprising at least one polymerase and at least one protein having a low isoelectric point, or at least one protein having a low isoelectric point and optionally at least one detergent, are provided.

In certain embodiments, methods and reaction mixtures for inhibiting inactivation of a polymerase during a polymerization and/or amplification reaction (e.g., thermal cycling process) include at least one protein having a low isoelectric point in the reaction mixture. In certain embodiments, methods and reaction mixtures for inhibiting inactivation of a polymerase during a polymerization and/or amplification reaction (e.g., thermal cycling process) include at least one protein having a low isoelectric point and optionally at least one detergent in the reaction mixture. In certain embodiments, the at least one protein having a low isoelectric point may substitute for a detergent in a polymerization and/or amplification reaction. In certain embodiments, the reaction mixture includes at least one protein having a low isoelectric point and is substantially free of detergent. In certain embodiments, methods and reaction mixtures are provided such that polymerization and/or amplification of a target nucleic acid occurs in the presence of at least one protein having a low isoelectric point, and wherein the polymerization and/or amplification of the target nucleic acid does not substantially occur in the absence of the at least one protein having a low isoelectric point.

In certain embodiments, methods for providing an enzyme having polymerase activity and at least one protein having a low isoelectric point, and combining the same to form a reaction mixture that stabilizes the polymerase activity of the enzyme are provided herein. In some embodiments, the methods include providing an enzyme having polymerase activity and at least one protein having a low isoelectric point, and optionally at least one detergent, and combining the same to form a reaction mixture that stabilizes the polymerase activity of the enzyme. In some embodiments, the methods include providing an enzyme having polymerase activity and at least one protein having a low isoelectric point, and combining the same to form a reaction mixture that is free of detergent and that stabilizes the polymerase activity of the enzyme. In certain embodiments, the methods described herein provide stabilization of the polymerase activity with at least one protein having a low isoelectric point such that the stabilized polymerase has an activity that is similar to (e.g., approximately the same) or greater than activity when stabilized by a detergent, such as NP-40, Tween® 20, and/or a detergent of Formula I.

In certain embodiments, the at least one protein having a low isoelectric point, or at least one protein having a low isoelectric point and optionally at least one detergent, or at least one protein having a low isoelectric point and is free of detergent, wherein the reaction mixture reduces the inhibition of the activity of a polymerase therein by, for example, other components of the reaction mixture. In certain embodiments, the polymerase is thermostable. In certain embodiments, the methods described herein provide increased amplification and/or polymerization efficiency with at least one protein having a low isoelectric point such that the amplification and/or polymerization efficiency is similar to (e.g., approximately the same) or greater than the amplification and/or polymerization efficiency with a detergent such as, for example, NP-40, Tween® 20, and/or a detergent of Formula I. The amplification and/or polymerization efficiency may be determined by various methods known in the art, including, but not limited to, determination of calibration dilution curves and slope calculation, determination using qBase software as described in Hellemans et al., *Genome Biology* 8:R19 (2007), determination using the delta delta Cq (ΔΔCq) calculation as described by Livak and Schmittgen, *Methods* 25:402 (2001), or by the method as described by Pfaffl, *Nucl. Acids Res.* 29:e45 (2001), all of which are herein incorporated by reference in their entirety. In some embodiments, the at least one protein having a low isoelectric point described herein may substitute for a detergent in an amplification reaction. In certain embodiments, the reaction mixture includes at least one protein having a low isoelectric point and is substantially free of detergent. In certain embodiments, methods and reaction mixtures are provided such that polymerization and/or amplification of the target nucleic acid occurs in the presence of at least one protein having a low isoelectric point, and wherein the polymerization and/or amplification of the target nucleic acid does not substantially occur in the absence of the at least one protein having a low isoelectric point. Target nucleic acids may be polymerized and/or amplified using any of a variety of reactions and systems.

In certain embodiments, compositions comprising a polymerase and, for example, at least one protein having a low isoelectric point are also provided herein. In certain embodiments, compositions comprising a polymerase and, for example, at least one protein having a low isoelectric point, and optionally at least one detergent, are provided herein. In certain embodiments, compositions comprising a polymerase and, for example, at least one protein having a low isoelectric point, wherein the composition is substantially free of detergent are provided herein. Kits comprising the components of such reaction mixtures and optionally also other reagents necessary for carrying out such methods or preparing such mixtures are also provided.

In some embodiments, a "protein having a low isoelectric point" may have an isoelectric point of, for example, between about 3 and about 8 and/or between about any of 3.0-3.1, 3.1-3.2, 3.3-3.4, 3.4-3.5, 3.5-3.6, 3.6-3.7, 3.7-3.8, 3.8-3.9, 3.9-4.0, 4.0-4.1, 4.1-4.2, 4.3-4.4, 4.4-4.5, 4.5-4.6, 4.6-4.7, 4.7-4.8, 4.8-4.9, 4.9-5.0, 5.0-5.1, 5.1-5.2, 5.3-5.4, 5.4-5.5, 5.5-5.6, 5.6-5.7, 5.7-5.8, 5.8-5.9, 5.9-6.0, 6.0-6.1, 6.1-6.2, 6.3-6.4, 6.4-6.5, 6.5-6.6, 6.6-6.7, 6.7-6.8, 6.8-6.9, 6.9-7.0, 7.0-7.1, 7.1-7.2, 7.3-7.4, 7.4-7.5, 7.5-7.6, 7.6-7.7, 7.7-7.8, 7.8-7.9, and 7.9-8.0. In one embodiment, the isoelectric point is about any of 4.2-4.5, 4.5, 4.6, 4.7, 4.7-5.2, 5.2-5.6, 5.29, or 6.8-7.3. In some embodiments, the isoelectric point may be less than about 5.29. In some embodiments, the isoelectric point may be 4.46. Exemplary proteins having low isoelectric points may be, for example, BSA, β-lactoglobulin, apomyoglobin, α-lactoalbumin, apotransferrin, α-acid glycoprotein, β-casein, a protein having an isoelectric point of less than 8 when in a PCR reaction mixture. In certain embodiments, a protein having a low isoelectric point has a negative charge when in a PCR reaction mixture.

In certain embodiments, the "effective concentration" (e.g., the amount that will support and/or improve a polymerization and/or amplification reaction such as PCR) of the at least one protein having a low isoelectric point may be, for example, from about 0.001 to about 1 mg/ml (e.g., about any of 0.0025, 0.005, 0.0075, 0.01, 0.025, 0.05, 0.075, 0.1, 0.25, 0.5, 0.75, or 1 mg/ml). In some embodiments, more than one protein having a low isoelectric point may be used. The effective concentrations listed above may refer to the total concentration of all of such proteins in a reaction mixture, or may refer to each of such proteins individually. Thus, in some embodiments, each of the proteins may be included at a concentration of, for example, 0.001 mg/ml to about 1 mg/ml, or the total of all of such proteins in the reaction mixture may be from, for example, 0.001 mg/ml to about 1 mg/ml. Other embodiments, including effective concentrations of the at least one protein having a low isoelectric point may also be suitable as would be understood by one of skill in the art.

Typically, the at least one protein having a low isoelectric point is included in a reaction mixture prior to initiation of polymerization and/or amplification but, in some embodiments, it may be introduced after initiation of the reaction. In some embodiments, it may be added to the reaction mixture as a separate component (e.g., separate from the polymerase). In others, it may be part of a mixture that includes the polymerase (e.g., as part of a "master mix") which is combined with the target nucleic acid prior to polymerization and/or amplification. Such a mixture may also be added during polymerization and/or amplification as well.

As described above, in some embodiments, methods for increasing the efficiency of a polymerase are provided. The efficiency of a polymerase may be increased with respect to, for example, either or both amplification efficiency or polymerization efficiency. This may be accomplished by, for example, stabilizing the polymerase and/or decreasing inhibition of the activity thereof by including a protein having a low isoelectric point (e.g., substituting for a detergent), or a protein having a low isoelectric point and optionally a detergent, in the polymerization and/or amplification reaction mixture (e.g., at least during the polymerization and/or amplification steps thereof).

As used herein, "amplification efficiency" may refer to any product that may be quantified to determine copy number (e.g., the term may refer to a PCR amplicon, an LCR ligation product, and/or similar product). Whether a particular protein having a low isoelectric point functions as desired in a particular amplification reaction may be determined by carrying out at least two separate amplification reactions, each reaction being carried out in the absence and presence, respectively, of at least one such protein and quantifying amplification that occurs in each reaction. Various concentrations or combinations of such proteins (e.g., with or without additional reagents such as detergents) may also be tested in separate reaction mixtures to determine the effect on amplification efficiency. Efficiency may be calculated as, for example, cycle threshold value (e.g., Cq) or amplification variability (e.g., delta Rn or ΔRn). A lower Cq and/or delta Rn value indicates a more efficient amplification reaction. The amplification and/or polymerization efficiency may be determined by various methods known in the art, including, but not limited to, determination of calibration dilution curves and slope calculation, determination using qBase software as described in Hellemans et al., *Genome Biology* 8:R19 (2007), determination using the delta delta Cq (ΔΔCq) calculation as described by Livak and Schmittgen, *Methods* 25:402 (2001), or by the method as described by Pfaffl, *Nucl. Acids Res.* 29:e45 (2001), all of which are herein incorporated by reference in their entirety. "Polymerization efficiency" may also be improved, with or without an improvement in amplification efficiency, using at least one protein having a low isoelectric point. Polymerization efficiency may be measured by conducting a nucleic acid polymerization assay in the absence or presence of at least one protein having a low isoelectric point (e.g., with or without additional reagents such as detergents), quantifying the amount of polymerization, and comparing the amount of polymerization that occurs in each reaction. Other methods for determining amplification efficiency and polymerization efficiency are known in the art and may be suitable for use as would be understood by one of skill in the art.

In certain embodiments, the methods may comprise mixing a target nucleic acid with at least one polymerase, at least one primer, dNTPs, and at least one protein having a low isoelectric point; and, allowing amplification of said target nucleic acid to occur by subjecting the mixture to thermal cycling. In certain embodiments, the methods may comprise mixing a target nucleic acid with at least one polymerase, at least one primer, dNTPs, at least one protein having a low isoelectric point, and optionally at least one detergent; and, allowing amplification of said target nucleic acid to occur by subjecting the mixture to thermal cycling. In certain embodiments, the methods may further comprise detecting and/or quantitating a target nucleic acid in a sample by forming a reaction mixture comprising at least one polymerase, a primer, dNTPs, at least one protein having a low isoelectric point, and a detectable label; subjecting said reaction mixture to nucleic acid amplification reaction conditions which amplify said target nucleic acid; and, detecting a signal generated from said detectable label indicative of the presence and/or amount of said target nucleic acid said sample.

In certain embodiments, the methods may further comprise detecting and/or quantitating a target nucleic acid in a sample by forming a reaction mixture comprising at least one polymerase, a primer, dNTPs, at least one protein having a low isoelectric point, and optionally at least one detergent, and a detectable label; subjecting said reaction mixture to nucleic acid amplification reaction conditions which amplify said target nucleic acid; and, detecting a signal generated from said detectable label indicative of the presence and/or amount of said target nucleic acid said sample. In certain embodiments, the methods may further comprise detecting and/or quantitating a target nucleic acid in a sample by forming a reaction mixture comprising at least one polymerase, a primer, dNTPs, at least one protein having a low isoelectric point and is free of detergent, and a detectable label; subjecting said reaction mixture to nucleic acid amplification reaction conditions which amplify said target nucleic acid; and, detecting a signal generated from said detectable label indicative of the presence and/or amount of said target nucleic acid said sample. In certain embodiments, the methods include, inhibiting inactivation of a polymerase in a thermal cycling process by contacting the polymerase with at least one protein having a low isoelectric point during the thermal cycling process. In certain embodiments, the methods comprise providing an enzyme having polymerase activity and at least one protein having a low isoelectric point and combining said enzyme and said protein to form a reaction mixture that stabilizes the polymerase activity of said enzyme. In any of these embodiments, the enzyme and/or polymerase may be, for example, a thermostable polymerase. In some embodiments, the methods include providing an enzyme having polymerase activity and at least one protein having a low isoelectric point, and combining the same to form a reaction mixture that is free of detergent and that stabilizes the polymerase activity of the enzyme. In certain embodiments, the methods described herein provide stabilization of the polymerase activity with at least one protein having a low isoelectric point such that the stabilized polymerase has an activity that is similar to (e.g., approximately the same) or greater than activity when stabilized by a detergent, such as NP-40, Tween® 20, and/or a detergent of Formula I.

As described above, one or more detergents may be included along with the at least one protein having a low isoelectric point. The ability of the at least one protein having a low isoelectric point to stabilize, decrease inhibition of (e.g., by other components in a reaction mixture), or improve the polymerization and/or amplification efficiency of a polymerase may also be compared to a detergent. Exemplary detergents may include, for example, NP-40, Tween® 20, and/or any of those described in U.S. Patent Application Ser. No. 61/351,796, U.S. Patent Application Ser. No. 61/433,499, U.S. Patent Publication No. 2008-0064071 A1 (U.S. patent application Ser. No. 11/828,107), U.S. Patent Publication No. 2008-0145910 A1 (U.S. patent application Ser. No. 11/612,776), U.S. Pat. No. 5,871,975, U.S. Pat. No. 6,127,155, and U.S. Pat. No. 6,242,235 (U.S. patent application Ser. No. 09/338,174), all of which being hereby incorporated in their entirety into this disclosure, and/or a detergent of Formula I. Formula I is shown below:

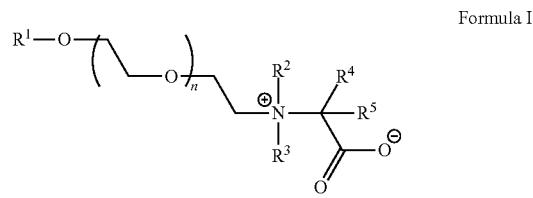

Formula I wherein:
R$^1$ is H or any alkyl chain from C$_5$ to C$_{30}$, including but not limited to C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$ C$_{23}$ C$_{24}$ C$_{25}$ C$_{26}$ C$_{27}$ C$_{28}$ C$_{29}$ C$_{30}$, and, aryl, substituted aryl, phenyl, substituted phenyl, where the substituted aryl or substituted phenyl is substituted by an alkyl chain from C$_5$ to C$_{30}$, including but not limited to C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$;
R$^2$ and R$^3$ are selected from the group consisting of: H, CH$_3$, CH(CH$_3$)$_2$, CH$_2$(C$_6$H$_5$), C(CH$_3$)$_3$;
R$^4$ and R$^5$ are selected from the group consisting of: H, CH$_3$, CH(CH$_3$)$_2$, C$_6$H$_5$, CH$_2$(C$_6$H$_5$), C(CH$_3$)$_3$, CH$_2$CH(CH$_3$)$_2$, CHCH$_2$CH(CH$_3$)$_2$, CH$_2$C$_6$H$_5$OH, CH$_2$C=CH NH(C$_6$H$_5$), CH$_2$C=CHN=CHNH, CH$_2$COOH, CH$_2$CONH$_2$, (CH$_2$)$_2$CONH$_2$, (CH$_2$)$_2$COOH, CH$_2$SH, (CH$_2$)$_n$NH, (CH$_2$)$_n$N, (CH$_2$)$_n$N, CH$_2$OH, CH(OH)CH$_3$, (CH$_2$)$_2$SCH$_3$, (CH$_2$)$_3$NHC(NH$_2$)=NH; and,
n independently is any positive integer, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

In some embodiments, R$^1$ is a C$_8$ alkyl chain. In other embodiments, R$^1$ is a C$_{16}$ alkyl chain.

Any of such detergents, among others, may be combined with at least one protein having a low isoelectric point. The ability of such proteins to stabilize a polymerase, of a polymerase (e.g., by other components in a reaction mixture), or increase the polymerization and/or amplification efficiency of a polymerase may also be compared to similar activities provided by such detergents.

As used herein, the terms "amplification", "nucleic acid amplification", "polymerizing", and/or "amplifying" may refer to the production of multiple copies of a nucleic acid template, or the production of multiple nucleic acid sequence copies that are complementary to the nucleic acid template. The terms may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid. The term "amplification reaction mixture" and/or "master mix" may refer to an aqueous solution comprising the various (some or all) reagents used to amplify a target nucleic acid. Such reactions may also be performed using solid supports (e.g., an array). The reactions may also be performed in single or multiplex format as desired by the user. These reaction mixtures may include, for example, enzymes (e.g., polymerase, uracil DNA glycosylase (UDG, AmpErase® UNG (Life Technologies Corp., Carlsbad, Calif.)), aqueous buffers, salts, amplification primers, target nucleic acid, passive reference nucleic acids (e.g., ROX) (e.g., to correct for inter-well variation caused by slight differences in reaction volume), nucleoside triphosphates, an additive having a "molecular crowding" effect (e.g., one of more types of large polymer molecule such as polyethylene glycol, fish gelatin, and/or DNA). Depending upon the context, the mixture may be either a complete or incomplete amplification reaction mixture (e.g., a master mix containing all or less than all of the components required to carry out an amplification reaction).

The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that the at least one protein having a low isoelectric point, or the at least one protein having a low isoelectric point and optionally a detergent, described herein should be effective in other types of nucleic acid amplification reactions, including both polymerase-mediated amplification reactions (such as helicase-dependent amplification (HAD), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see for example U.S. Pat. No. 6,797,470). For example, the novel detergents may be used in, for example, various ligation-mediated reactions, where for example, ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., PCT Publication No. WO 2006/081222), strand displacement (see, e.g., U.S. Pat. No. RE39007E), partial destruction of primer molecules (see, e.g., PCT Publication No. WO 2006/087574)), ligase chain reaction (LCR) (see, e.g., Wu, et al., *Genomics* 4: 560-569 (1990)), and/or Barany, et al. *Proc. Natl. Acad. Sci. USA* 88:189-193 (1991)), Qβ RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854,033; U.S. Patent Publication No. 2004/265897; Lizardi et al. *Nat. Genet.* 19: 225-232 (1998); and/or Banér et al. *Nucleic Acid Res.*, 26: 5073-5078 (1998)), and strand displacement amplification (SDA) (Little, et al. *Clin. Chem.* 45:777-784 (1999)), among others. These systems, along with the many other systems available to the skilled artisan, may be suitable for use in polymerizing and/or amplifying target nucleic acids for use as described herein.

Exemplary methods for polymerizing and/or amplifying nucleic acids include, for example, polymerase-mediated extension reactions. For instance, the polymerase-mediated extension reaction may be the polymerase chain reaction (PCR). In other embodiments, the nucleic acid amplification reaction is a multiplex reaction. For instance, exemplary methods for amplifying and detecting nucleic acids suitable for use as described herein are commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase displaces and/or digests and/or cleaves the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

Another exemplary system suitable for use as described herein utilizes double-stranded probes in displacement hybridization methods (see, e.g., Morrison et al. *Anal. Biochem.*, 18:231-244 (1989); and/or Li, et al. *Nucleic Acids Res.*, 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for amplifying and detecting target nucleic acids suitable for use as described herein involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher dye that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for amplifying RNA to double stranded DNA without temperature cycling. A NASBA reaction typically requires avian myeloblastosis virus (AMV), reverse transcriptase (RT), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpions™ system is another exemplary assay format that may be used in the methods described herein. Scorpions™ primers are bi-functional molecules in which a primer is covalently linked to the probe, along with a detectable label (e.g., a fluorophore) and a quencher. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., a hexaethylene glycol (HEG) monomer (Whitcombe, et al. *Nat. Biotech.* 17: 804-807 (1999)) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpions™ system may be used to examine and identify point mutations using multiple probes that may be differentially tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for molecular beacons are known in the art and would be suitable for use in the methods described herein.

The nucleic acid polymerases that may be employed in the disclosed nucleic acid polymerization and/or amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand may be complementary to the template strand. DNA polymerase may add free nucleotides to the 3'-hydroxyl end of the newly forming strand. It typically synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'-to-3' direction. Since DNA polymerase adds a nucleotide onto a pre-existing 3'-OH group, to begin a DNA synthesis reaction, the DNA polymerase needs a primer to which it may add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5'-to-3' exonuclease activity, a DNA polymerase having a reverse transcriptase activity, or a DNA polymerase having an endonuclease activity.

Suitable nucleic acid polymerases may also comprise holoenzymes, functional portions of the holoenzymes, chimeric polymerase, fusion polymerase, or any modified polymerase that may effectuate the synthesis of a nucleic acid molecule. Within this disclosure, a DNA polymerase may also include a polymerase, terminal transferase, reverse transcriptase, telomerase, and/or polynucleotide phosphorylase. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, η, ζ, ι, and/or κ; *E. coli* DNA polymerase I; *E. coli* DNA polymerase III alpha and/or epsilon subunits; *E. coli* polymerase IV, *E. coli* polymerase V; *T. aquaticus* DNA polymerase I; *B. stearothermophilus* DNA polymerase I; Euryarchaeota polymerases; terminal deoxynucleotidyl transferase (TdT); *S. cerevisiae* polymerase 4; translesion synthesis polymerases; reverse transcriptase; and/or telomerase. Non-limiting examples of suitable thermostable DNA polymerases that may be used include Taq, Tfl, Tfi, Pfu, and Vent™ DNA polymerases, any having reduced or insignificant 3' to 5' exonuclease activity (e.g., SuperScript™ DNA polymerase), and/or genetically engineered DNA polymerases (e.g., those having the active site mutation F667Y or the equivalent of F667Y (e.g., in Tth), AmpliTaq® FS, Thermo Sequenase™), Therminator I, Therminator II, Therminator III, Therminator Gamma (all available from New England Biolabs, Beverly, Mass.), fusion polymerases, and/or any derivatives and fragments thereof. Other nucleic acid polymerases may also be suitable as would be understood by one of skill in the art.

In some embodiments, the reaction mixture may further comprise a detectable label. The methods may also include one or more steps for detecting the detectable label to quantitate the amplified nucleic acid. As used herein, the term "detectable label" refers to any of a variety of signaling molecules indicative of amplification. For example, SYBR® Green and other DNA-binding dyes are detectable labels. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos.

5,994,056; 6,171,785; and/or 6,814,934). Similarly, actinomycin D fluoresces red fluorescence when bound to single-stranded nucleic acids, and green when bound to double-stranded nucleic acids. And in another example, the photoreactive psoralen 4-aminomethyl-4-5',8-trimethylpsoralen (AMT) has been reported to exhibit decreased absorption at long wavelengths and fluorescence upon intercalation into double-stranded DNA (Johnson et al. *Photochem. & Photobiol.*, 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders as described herein such as Hoechst 33258, distamycin, netropsin) may also be suitable for use. For example, Hoechst 33258 (Searle, et al. *Nucl. Acids Res.* 18(13):3753-3762 (1990)) exhibits altered fluorescence with an increasing amount of target. Minor groove binders are described in more detail elsewhere herein.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. *J. Mol. Biol.* 68:21 (1972)), anthramycin, BOBO™-1, BOBO™-3, BO-PRO™-1, cbromomycin, DAPI (Kapuseinski, et al. *Nucl. Acids Res.* 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, *Nucl. Acids Res.* 18:3753-3762 (1990)), Hoechst 33342, homidium, JO-PRO™-1, LIZ dyes, LO-PRO™-1, mepacrine, mithramycin, NED dyes, netropsin, 4',6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX blue, SYTOX green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO®-1, and YOYO®-3 (Molecular Probes, Inc., Eugene, Oreg.), among others. SYBR® Green I (see, e.g., U.S. Pat. Nos. 5,436,134; 5,658,751; and/or 6,569,927), for example, has been used to monitor a PCR reactions. Other DNA binding dyes may also be suitable as would be understood by one of skill in the art.

For use as described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments, the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorphore (e.g., a chemical group that may be excited by light to emit fluorescence or phosphorescence), "acceptor dyes" capable of quenching a fluorescent signal from a fluorescent donor dye, and the like. Suitable detectable labels may include, for example, fluorosceins (e.g., 5-carboxy-2,7-dichlorofluorescein; 5-Carboxyfluorescein (5-FAM); 5-HAT (5-Hydroxy Tryptamine); 6-JOE; 6-carboxyfluorescein (6-FAM); FITC; 6-carboxy-1,4-dichloro-2',7'-dichlorofluorescein (TET); 6-carboxy-1,4-dichloro-2',4',5',7'-tetrachlorofluorescein (HEX); 6-carboxy-4',5'-dichloro-2',7'-dimethoxyfluorescein (JOE); Alexa Fluor® fluorophores (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (Fi-CRhR), fluorescent proteins (e.g., green fluorescent protein (e.g., GFP, EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor™ Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B and C, Sulphorhodamine G Extra, TAMRA (6-carboxytetramethylrhodamine), Tetramethylrhodamine (TRITC), WT), Texas Red, Texas Red-X, VIC and other labels described in, e.g., U.S. Patent Publication No. 2009/0197254 (incorporated herein by reference in its entirety), among others as would be known to those of skill in the art. Other detectable labels may also be used (see, e.g., U.S. Patent Publication No. 2009/0197254 (incorporated herein by reference in its entirety)), as would be known to those of skill in the art. Any of these systems and detectable labels, as well as many others, may be used to detect amplified target nucleic acids.

Some detectable labels may be sequence-based (also referred to herein as "locus-specific detectable label"), for example 5'-nuclease probes. Such probes may comprise one or more detectable labels. Various detectable labels are known in the art, for example (TaqMan® probes described herein (See also U.S. Pat. No. 5,538,848 (incorporated herein by reference in its entirety)) various stem-loop molecular beacons (See, e.g., U.S. Pat. Nos. 6,103,476 and 5,925,517 and Tyagi and Kramer, *Nat. Biotechnology* 14:303-308 (1996)), stemless or linear beacons (See, e.g., PCT Publication No. WO 99/21881; U.S. Pat. No. 6,485, 901), PNA Molecular Beacons™ (See, e.g., U.S. Pat. Nos. 6,355,421 and 6,593,091), linear PNA beacons (See, e.g., Kubista et al., *SPIE* 4264:53-58 (2001)), non-FRET probes (See, e.g., U.S. Pat. No. 6,150,097), Sunrise®/Amplifluor® probes (U.S. Pat. No. 6,548,250), stem-loop and duplex Scorpions™ probes (Solinas et al., *Nucleic Acids Research* 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes (Svanvik, et al. *Anal Biochem* 281:26-35 (2001)), self-assembled nanoparticle probes, ferrocene-modified probes (described, for example, in U.S. Pat. No. 6,485,901; Mhlanga et al., *Methods* 25:463-471 (2001); Whitcombe et al., *Nature Biotechnology* 17:804-807 (1999); Isacsson et al., *Molecular Cell Probes* 14:321-328 (2000); Svanvik et al., *Anal Biochem.* 281:26-35 (2000); Wolffs et al., *Biotechniques* 766:769-771 (2001); Tsourkas et al., *Nucleic Acids Research* 30:4208-4215 (2002); Riccelli et al., *Nucleic Acids Research* 30:4088-4093 (2002); Zhang et al., *Acta Biochimica et Biophysica Sinica (Shanghai).* 34:329-332 (2002); Maxwell et al., *J. Am. Chem. Soc.* 124:9606-9612 (2002); Broude et al., *Trends Biotechnol.* 20:249-56 (2002); Huang et al., *Chem Res. Toxicol.* 15:118-126 (2002); and Yu et al., *J. Am. Chem. Soc.* 14:11155-11161 (2001)), QuantiProbes® (www.qiagen.com), HyBeacons® (French, et al. *Mol. Cell. Probes* 15:363-374 (2001)), displacement probes (Li, et al. *Nucleic Acids Res.* 30:e5 (2002)), Hyb-Probes (Cardullo, et al. *PNAS USA* 85:8790-8794 (1988)), MGB Alert (www.nanogen.com), Q-PNA (Fiandaca, et al. *Genome Res.* 11:609-611 (2001)), Plexor (www.Promega.com), LUX™ primers (Nazarenko, et al. *Nucleic Acids Res.* 30:e37 (2002)), DzyNA primers (Todd, et al. *Clin. Chem.* 46:625-630 (2000)). Detectable labels may also comprise a non-detectable quencher moiety, such as, for example, black hole quenchers (Biosearch), Iowa Black® quencher (IDT), QSY quencher (Molecular Probes), and Dabsyl and Dabcyl sulfonate/carboxylate Quenchers (Epoch). Detectable labels may also comprise two probes, wherein for example a fluorophore is on one probe, and a quencher on the other, wherein hybridization of the two probes together on a target quenches the signal, or wherein hybridization on a target alters the signal signature via a change in fluorescence. Exemplary systems may also include FRET, salicylate/DTPA ligand systems (see, e.g., Oser et al. *Angew. Chem. Int. Engl.* 29(10):1167 (1990)), displacement hybridization, homologous probes, and/or assays described in European Patent No. EP 070685 and/or U.S. Pat. No. 6,238,927. Detectable labels may also comprise sulfonate derivatives of fluorescein dyes with $SO_3$ instead of the carboxylate group, phosphoramidite forms of fluorescein, phosphoramidite forms of Cy5 (available, for example, from Amersham). All references cited above are hereby incorporated herein by reference in their entirety.

The detergents and methods described herein may be useful for detecting and/or quantifying a variety of target nucleic acids from a test sample. A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, spinal fluid), a tissue sample, a food (e.g., meat) or beverage (e.g., milk) product, or the like. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods described herein may be also be used to detect rare alleles in the presence of wild type alleles (e.g., one mutant allele in the presence of $10^6$-$10^9$ wild type alleles). The methods are useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

Kits for performing the methods described herein are also provided. As used herein, the term "kit" refers to a packaged set of related components, typically one or more compounds or compositions. The kit may comprise a pair of oligonucleotides for amplifying at least one target nucleic acid from a sample, one or more detergents (e.g., novel and/or conventional detergents, or a mixture comprising any of the same) (See, for example, U.S. Patent Application Ser. No. 61/351, 796, U.S. Patent Application Ser. No. 61/433,499, U.S. Patent Publication No. 2008-0064071 A1 (U.S. patent application Ser. No. 11/828,107), U.S. Patent Publication No. 2008-0145910 A1 (U.S. patent application Ser. No. 11/612, 776), U.S. Pat. No. 5,871,975, U.S. Pat. No. 6,127,155, and U.S. Pat. No. 6,242,235 (U.S. patent application Ser. No. 09/338,174), all of which are hereby incorporated-by-reference in their entirety into this disclosure), a biocatalyst (e.g., DNA polymerase) and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. The kit optionally contains instructions for performing an amplification or polymerization assay according to embodiments of the methods disclosed herein. Other embodiments of particular systems and kits are also contemplated which would be understood by one of skill in the art.

To more clearly and concisely describe and point out the subject matter of the present disclosure, definitions are provided for specific terms, which are used in the description and the appended claims. Throughout the specification, exemplification of specific terms should be considered as non-limiting examples. For example, the singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Where necessary, ranges have been supplied, and those ranges are inclusive of all sub-ranges there between. The use of the singular may include the plural unless specifically stated otherwise or unless, as will be understood by one of skill in the art in light of the present disclosure, the singular is the only functional embodiment. Thus, for example, "a" may mean more than one, and "one embodiment" may mean that the description applies to multiple embodiments. The phrase "and/or" denotes a shorthand way of indicating that the specific combination is contemplated in combination and, separately, in the alternative.

It will be appreciated that there is an implied "about" prior to the temperatures, concentrations, times, etc. discussed in the present teachings, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the present disclosure.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

As used herein, the terms "nucleotide" or "nucleotide base" refer to a nucleoside phosphate. It includes, but is not limited to, a natural nucleotide, a synthetic nucleotide, a modified nucleotide, or a surrogate replacement moiety or universal nucleotide (e.g., inosine). The nucleoside phosphate may be a nucleoside monophosphate, a nucleoside diphosphate or a nucleoside triphosphate. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleoside triphosphate (dNTP) or a ribonucleoside triphosphate (NTP). The nucleotides may be represented using alphabetical letters (letter designation). For example, A denotes adenosine (i.e., a nucleotide containing the nucleobase, adenine), C denotes cytosine, G denotes guanosine, T denotes thymidine, U denotes uracil, and I denotes inosine. N represents any nucleotide (e.g., N may be any of A, C, G, T/U, or I). Naturally occurring and synthetic analogs may also be used, including for example hypoxanthine, 2-aminoadenine, 2-thiouracil, 2-thiothymine, 5-methylcytosine, N4-methylcytosine, 5,N4-ethencytosine, 4-aminopyrazolo[3,4-d]pyrimidine and 6-amino-4-hydroxy [3,4-d]pyrimidine, among others. The nucleotide units of the oligonucleotides may also have a cross-linking function (e.g. an alkylating agent).

As used herein, the term "oligonucleotide" or "polynucleotide" refers to an oligomer of nucleotide or derivatives thereof. The oligomers may be DNA, RNA, or analogues thereof (e.g., phosphorothioate analogue). The oligomers may also include modified bases, and/or backbones (e.g., modified phosphate linkage or modified sugar moiety). Non-limiting examples of synthetic backbones that confer stability and/or other advantages to the oligomers may include phosphorothioate linkages, peptide nucleic acid, locked nucleic acid (Singh, et al. *Chem Commun* 4:455-456 (1998)), xylose nucleic acid, and/or analogues thereof. Oligonucleotides may be any length "n." For example, n may be any of 1, 2, 4, 6, 8, 12, 16, 20, 22, 24, 26, 28, 30, 32, 34, 36, 38, 40 etc. number of nucleotides. The polynucleotide structure $(N)_n$ represents an oligonucleotide consisting of n number of nucleotides N (e.g., $(I)_8$ is representative of an oligonucleotide having the sequence IIIIIIII; or $(A)_{12}$ is representative of an oligonucleotide having the sequence AAAAAAAAAAAA). Other types of oligonucleotides or polynucleotides may also be suitable for use as would be understood to one of skill in the art from this disclosure.

As used herein, the term "nucleic acid" refers to polymers of nucleotides or derivatives thereof. As used herein, the term "target nucleic acid" refers to a nucleic acid that is desired to be amplified in a nucleic acid amplification reaction. For example, the target nucleic acid comprises a nucleic acid template.

As used herein, the term "globular protein" refers to a protein that has a roughly globe-like or spherical tertiary structure and is more or less soluble in aqueous solution. Globular proteins typically have the polar (hydrophobic) amino acid bound towards the molecule's interior, whereas the polar (hydrophilic) amino acids are bound outwards allowing dipole-dipole interactions with the solvent. Globular proteins include, for example, albumins, including, but not limited to, bovine serum albumin, β-lactoglobulin, apomyoglobin, and α-lactoalbumin.

As used herein, the term "sequence" refers to a nucleotide sequence of an oligonucleotide or a nucleic acid. Throughout the specification, whenever an oligonucleotide/nucleic acid is represented by a sequence of letters, the nucleotides are in 5' to 3' order from left to right. For example, an oligonucleotide represented by a sequence $(I)_n(A)_n$ wherein n=1, 2, 3, 4 and so on, represents an oligonucleotide where the 5' terminal nucleotide(s) is inosine and the 3' terminal nucleotide(s) is adenosine.

As used herein the term "reaction mixture" refers to the combination of reagents or reagent solutions, which are used to carry out a chemical analysis or a biological assay. In some embodiments, the reaction mixture comprises all necessary components to carry out a nucleic acid (e.g., DNA, RNA) polymerization and/or amplification reaction. As described above, such reaction mixtures may include at least one amplification primer or primer pair suitable for amplifying a nucleic acid sequence of interest, the mixtures also containing at least one protein having a low isoelectric point, or at least one protein having a low isoelectric point and optionally at least one detergent. As described above, such reaction mixtures may include at least one protein having a low isoelectric point that may substitute for a detergent. In certain embodiments, the reaction mixture includes at least one protein having a low isoelectric point and is substantially free of detergent. In certain embodiments, methods and reaction mixtures are provided such that polymerization and/or amplification of the target nucleic acid occurs in the presence of at least one protein having a low isoelectric point, and wherein the polymerization and/or amplification of the target nucleic acid does not substantially occur in the absence of the at least one protein having a low isoelectric point.

As described above, a suitable reaction mixture may also include a "master mix" containing the components (e.g., typically not including the primer pair) needed to perform an amplification reaction. The master mix may include or be combined with one or more proteins having a low isoelectric point, or one or more proteins having a low isoelectric point and optionally at least one detergent, or one or more proteins having a low isoelectric point and is free of detergent, to form a reaction mixture. Other embodiments of reaction mixtures are also contemplated herein as would be understood by one of skill in the art.

As used herein, the terms "reagent solution" or "solution suitable for performing a nucleic acid synthesis reaction" refer to any or all solutions, which are typically used to perform polymerization and/or amplification reactions. These include, but are not limited to, solutions used in DNA and/or RNA polymerization and/or amplification reactions (e.g., including reverse transcriptase and other reactions) or the like. The solutions suitable for nucleic acid (e.g., DNA, RNA) synthesis reaction may comprise buffer, salts, and/or nucleotides. It may further comprise primers and/or nucleic acid (e.g., DNA, RNA) templates to be amplified. One or more reagent solutions are typically included in the reactions mixtures or master mixes described herein.

As used herein, the term "primer" or "primer sequence" refers to a short linear oligonucleotide that hybridizes to a target nucleic acid sequence (e.g., a DNA template to be amplified) to prime a nucleic acid synthesis reaction. The primer may be a RNA oligonucleotide, a DNA oligonucleotide, or a chimeric sequence (e.g., comprising RNA and DNA). The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about any of, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, (and so on) nucleotides.

Certain embodiments are further described in the following examples. These embodiments are provided as examples only and are not intended to limit the scope of the disclosure or claims in any way.

EXAMPLES

Example 1

Various proteins were tested for their ability to support nucleic acid amplification by a polymerase (see FIGS. 1-18). Nucleic acid targets were amplified by PCR in the presence of the indicated protein and compared to PCR carried out in the presence of 0.002% Dt4 ("D4") or Tween® 20 (0.1%) alone as positive controls. The proteins were tested at 0.1 mg/ml and 0.5 mg/ml. Taq and Tfi DNA polymerases were each tested separately (0.2 U/µL) using the LUX™ (Tfi, Taq) and TaqMan® (Taq) assays. Taq and Tfi are recombinant protein expressed in E. coli. PCR conditions were 95° C. for 20 seconds; 40 cycles of 3 seconds at 95° C., 30 seconds at 60° C., in a real-time PCR instrument (Applied Biosystems 7500 Fast Real-Time PCR System or equivalent). A summary of the proteins tested for their ability to improve PCR amplification is shown in Table 1.

TABLE 1

| Protein | Isoelectric point (iep) | PCR amplification | Modifications | FIGS. |
|---|---|---|---|---|
| α-acid glycoprotein | 3 | +/− | glycosylated | 1, 13, 14 |
| acetylated BSA | <4 | − | acetylated | 2, 15, 16 |
| Phosvitin | 4 | +/− | phosphorylated | N/A |
| α-lactoalbumin | 4.2 to 4.5 | + | | 3, 11, 12 |
| α-casein | 4.46 | + | | N/A |
| β-casein | 4.5 | + | | 4, 13, 14 |
| Ovalbumin | 4.6 | + | | N/A |
| BSA | 4.7 | + | | 5A-K, 15, 16 |
| β-lactoglobulin | 4.7 to 5.2 | + | | N/A |
| Apotransferrin | 5.2-5.6 | + | | 6, 13, 14 |
| Actin | 5.29 | + | | N/A |
| IgG | 6.4 to 9 | − | disulfide bond | N/A |
| Apomyoglobin | 6.8 to 7.3 | + | | 7, 11, 12 |
| Gelatin | 7.0-9.0 | − | glycosylated | N/A |
| Avidin | 10.5 | − | | 8, 11, 12 |
| cytochrome C | 10-10.5 | − | | 9, 15, 16 |
| t11k synthetic peptide | N/A | − | | |
| v12k synthetic peptide | N/A | − | | |
| no detergent or protein | N/A | − | | 10A, 17, 18 |
| Tween 20 | N/A | + | | 10B, 17, 18 |

As described above and illustrated in the Figures, polypeptides having an isoelectric point of between about 3 and about 8 were effective substitutes for 0.1% Tween® 20. Thus, the use of these proteins may alleviate the need for surfactant in PCR reactions perhaps by stabilizing the Taq and/or Tfi polymerases.

Figure 5A:
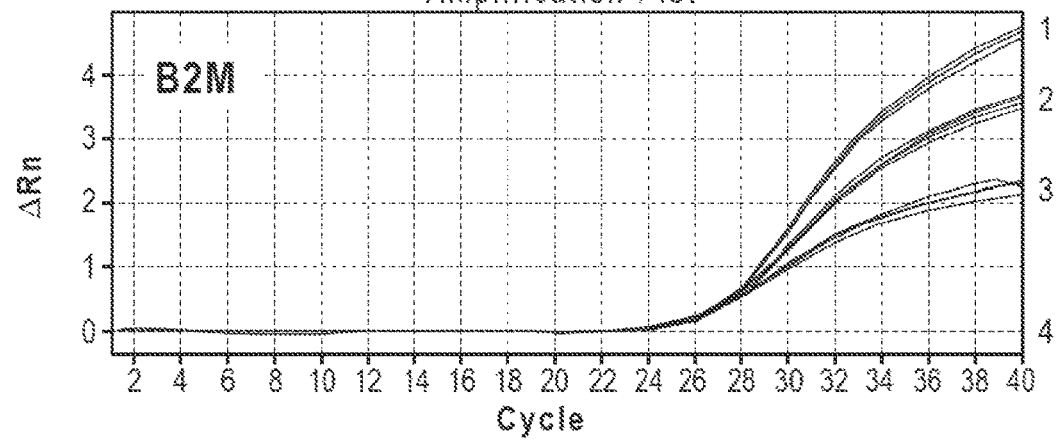
FIGS. 5A through 5K. A comparison of amplification reactions using bovine serum albumin (BSA), Dt4 and Tween® 20 according to certain exemplary embodiments of the methods and compositions disclosed herein. A. Use of bovine serum albumin (BSA) in amplification reactions of B2M, glyceraldehyde 3-phosphate dehydrogenase (GAPDH) or ribosomal protein, large P0 (RPLP0), compared to Dt4 and Tween® 20. B-E. Use of bovine serum albumin (BSA) in amplification reactions of phosphoglycerate kinase 1 (PGK1), HPRT1, GUSB or GAPDH, compared to Dt4, Dt4 and BSA, and Tween® 20. F-I. Further use of bovine serum albumin (BSA) in amplification reactions of actin-beta (ACTB), B2M, peptidyl prolyl isomerase A (PPIA) or large ribosomal protein (RPLPO), compared to Dt4, Dt4 and BSA, and Tween® 20. J. Use of bovine serum albumin (BSA) in amplification reactions of GAPDH with Taq or Tfi polymerases. K. Use of bovine serum albumin (BSA) in amplification reactions of HPRT1, GUSB or B2M, compared to Dt4, Dt4 and BSA, and Tween® 20.
Figure 5A:
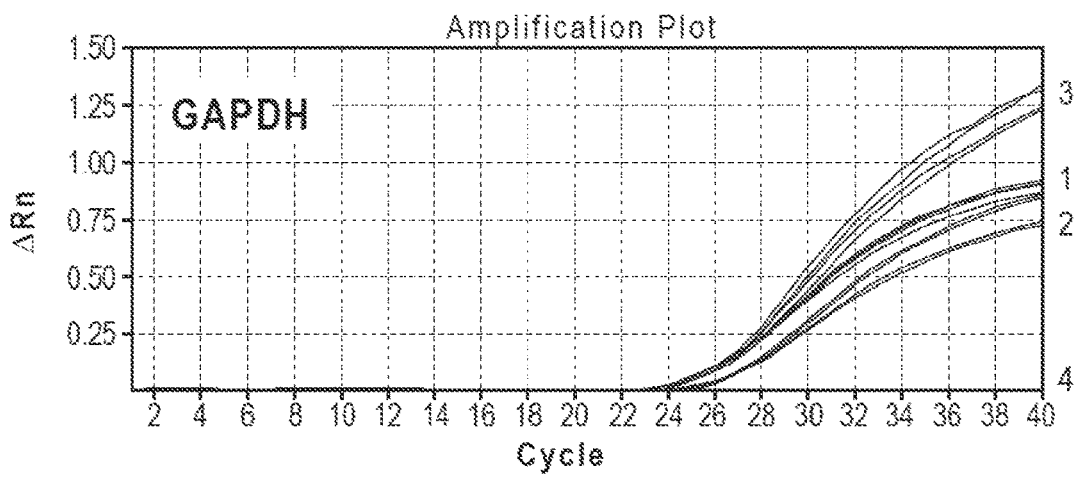
Figure 5A:
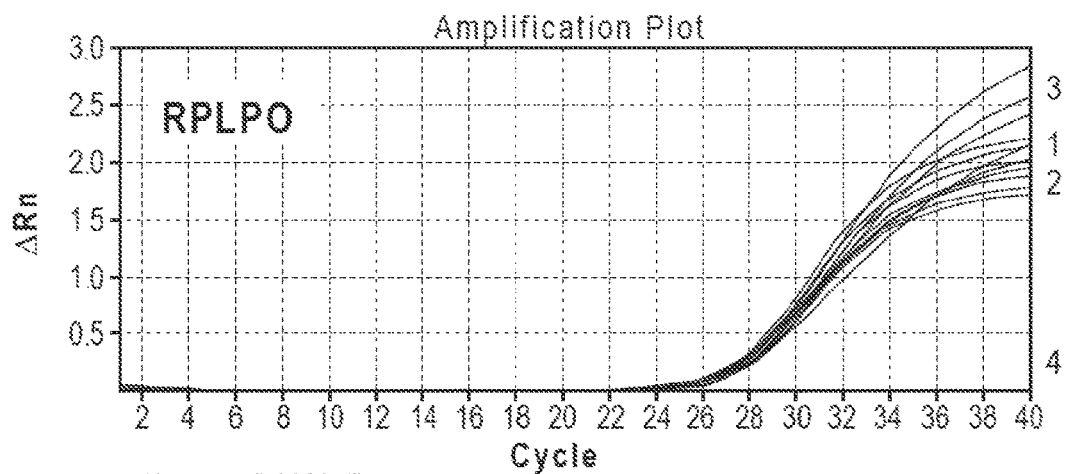
Figure 5B:
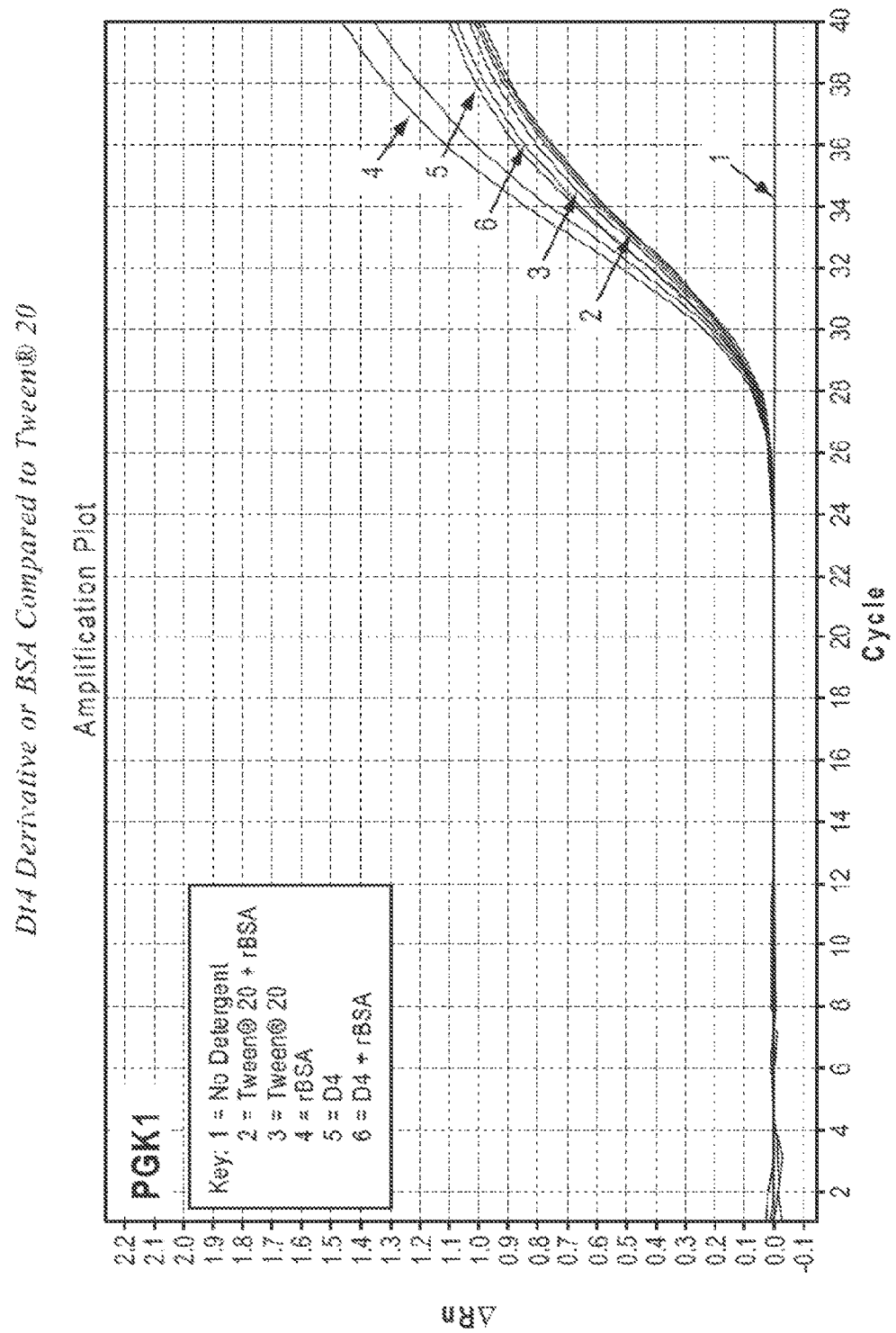
Figure 5C:
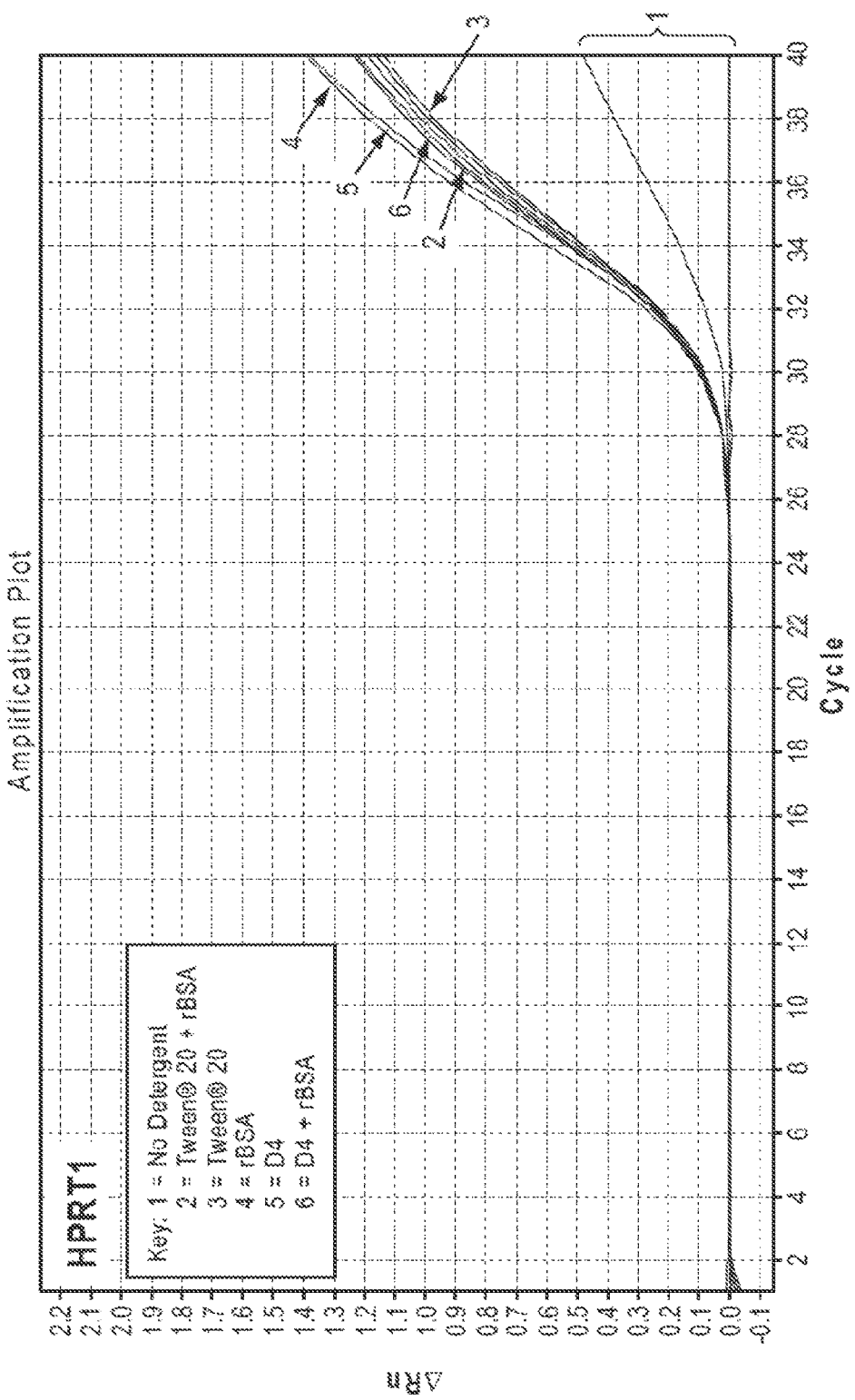
Figure 5D:
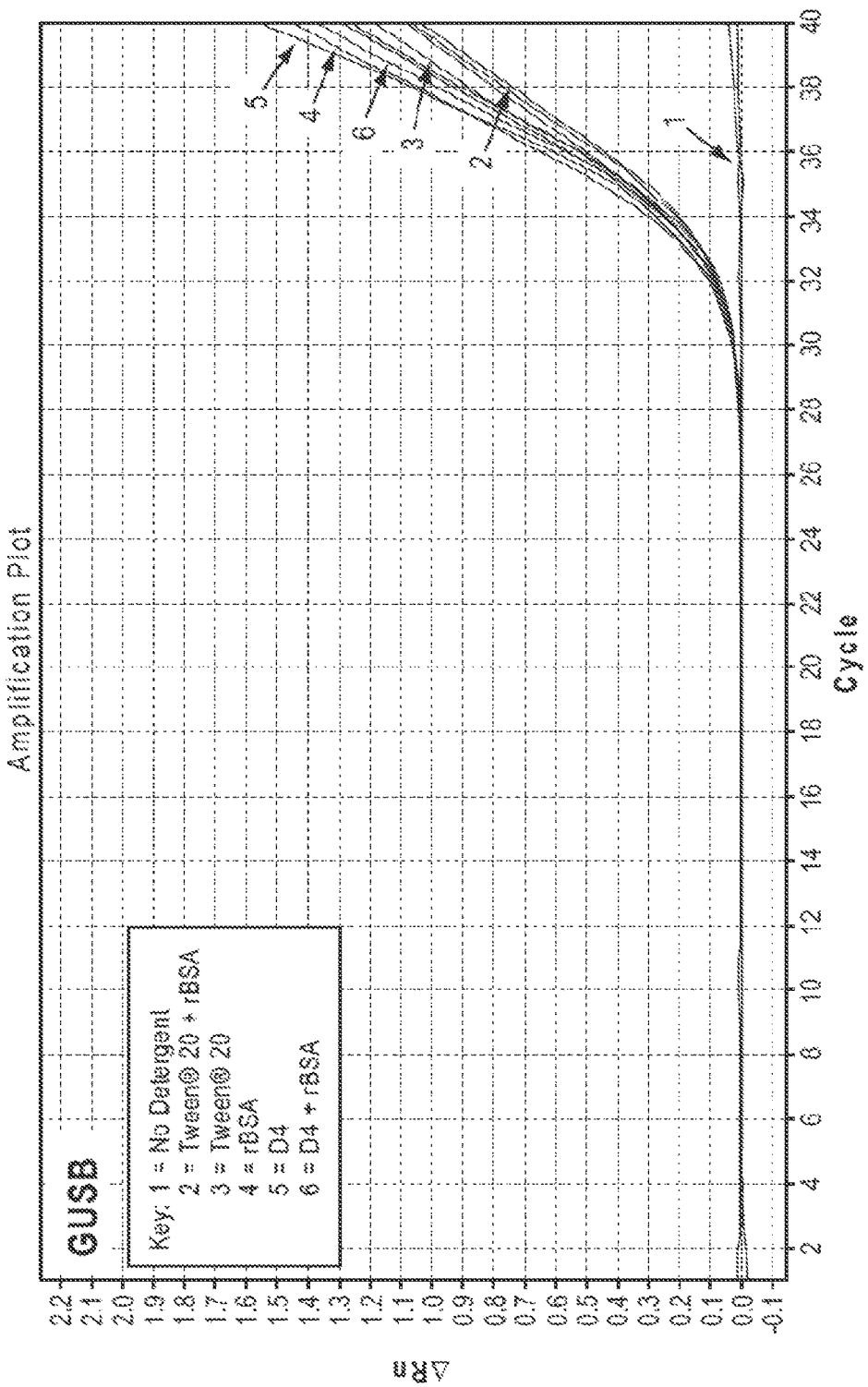
Figure 5E:
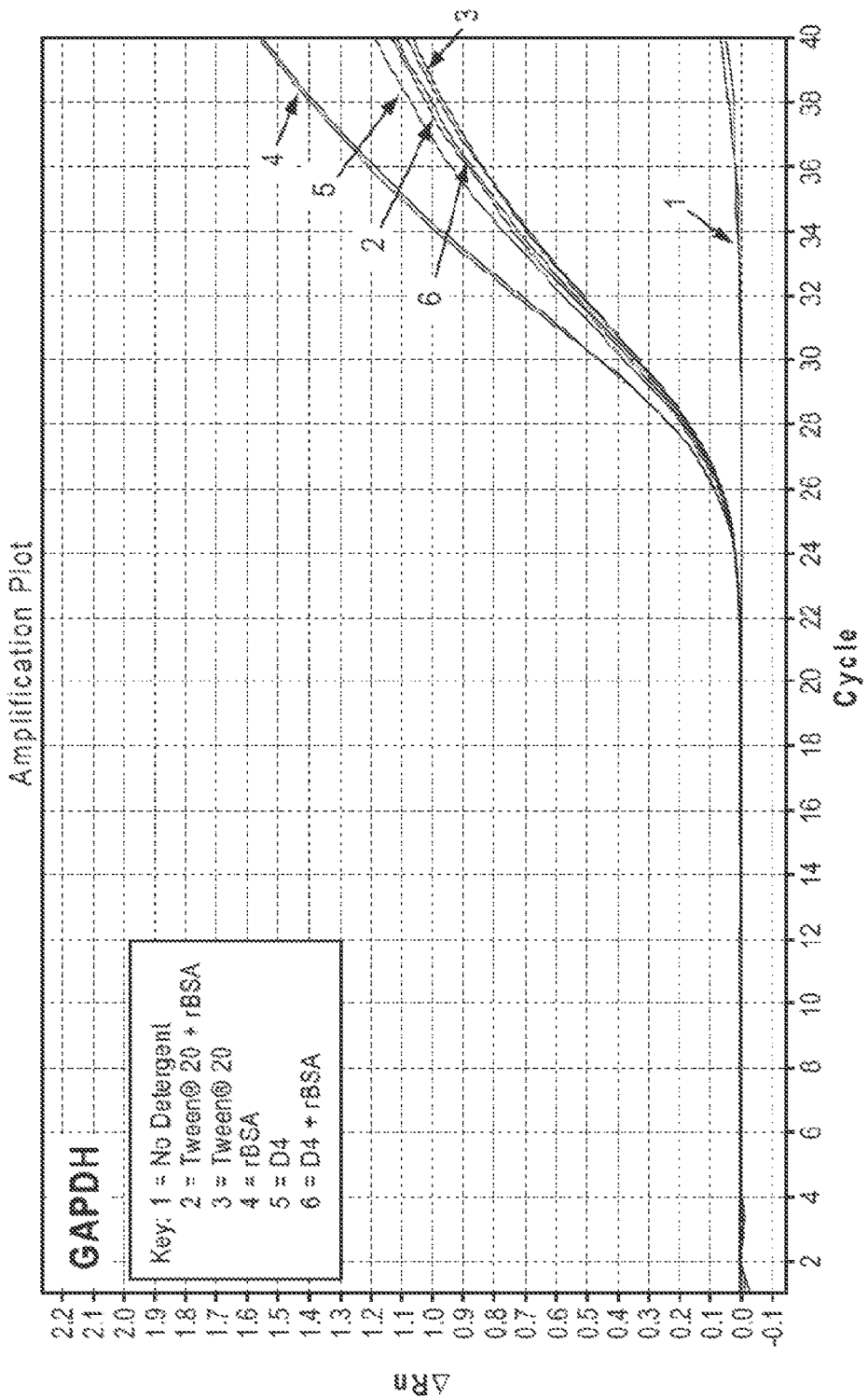
Figure 5F:
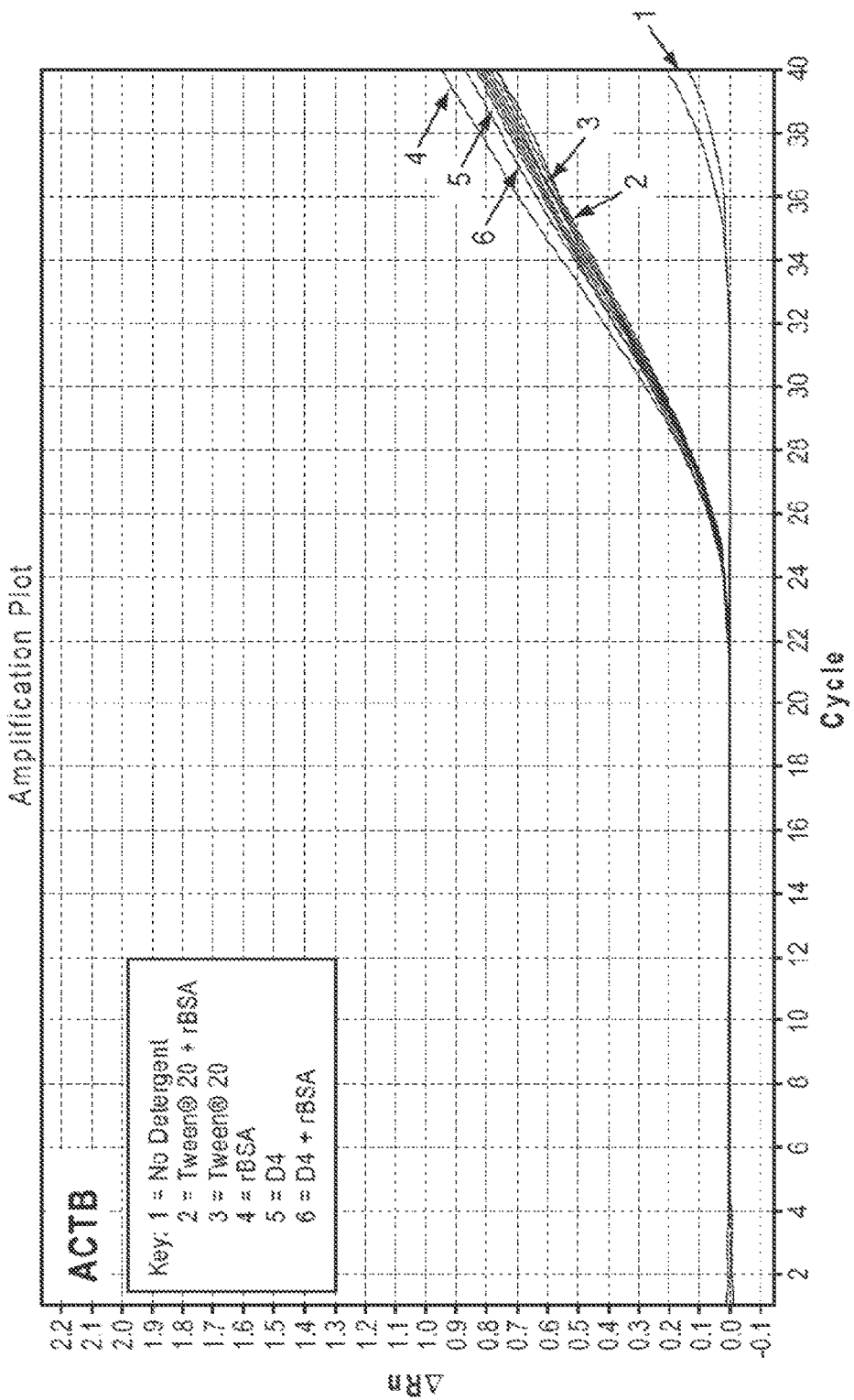
Figure 5G:
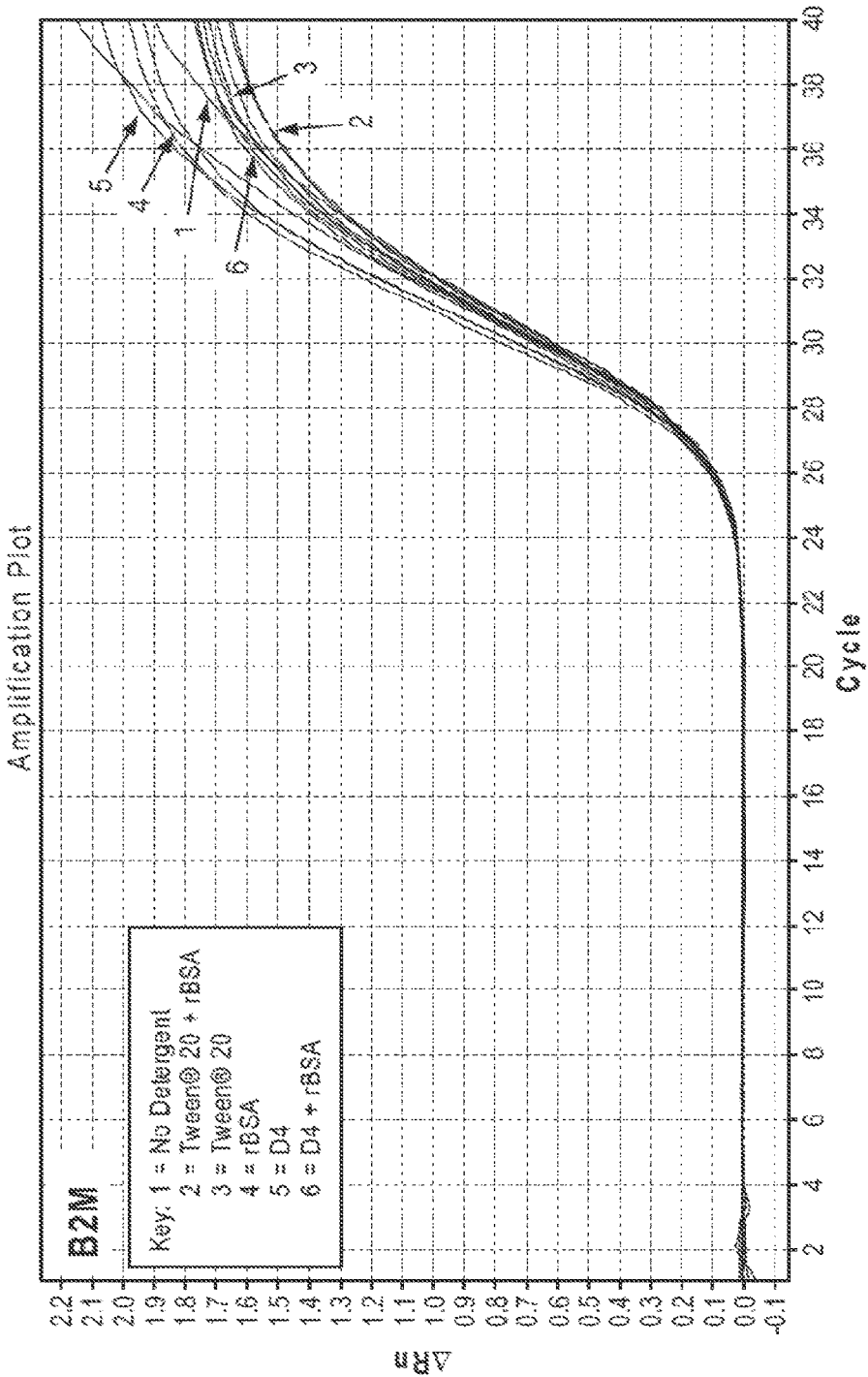
Figure 5H:
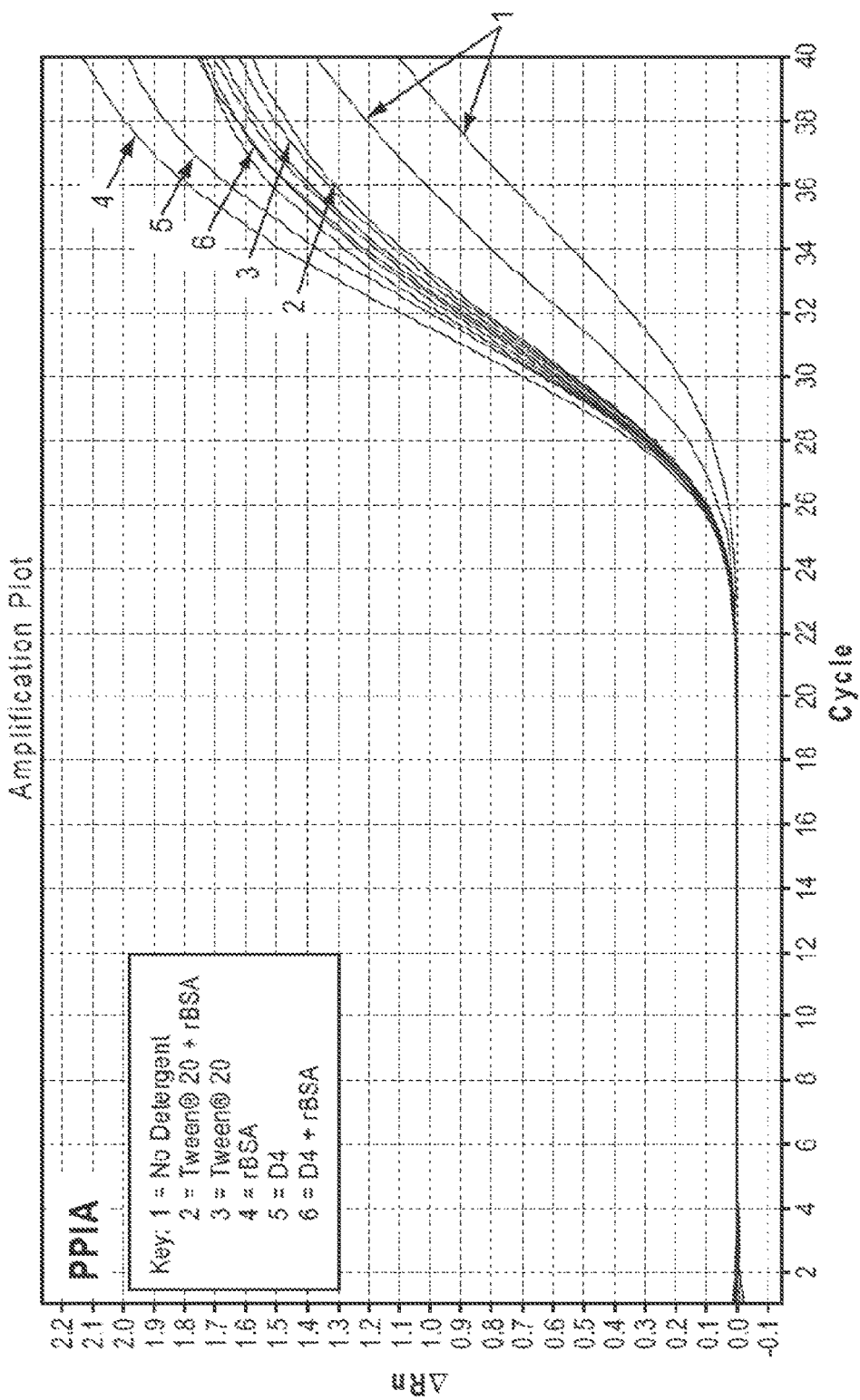
Figure 5I:
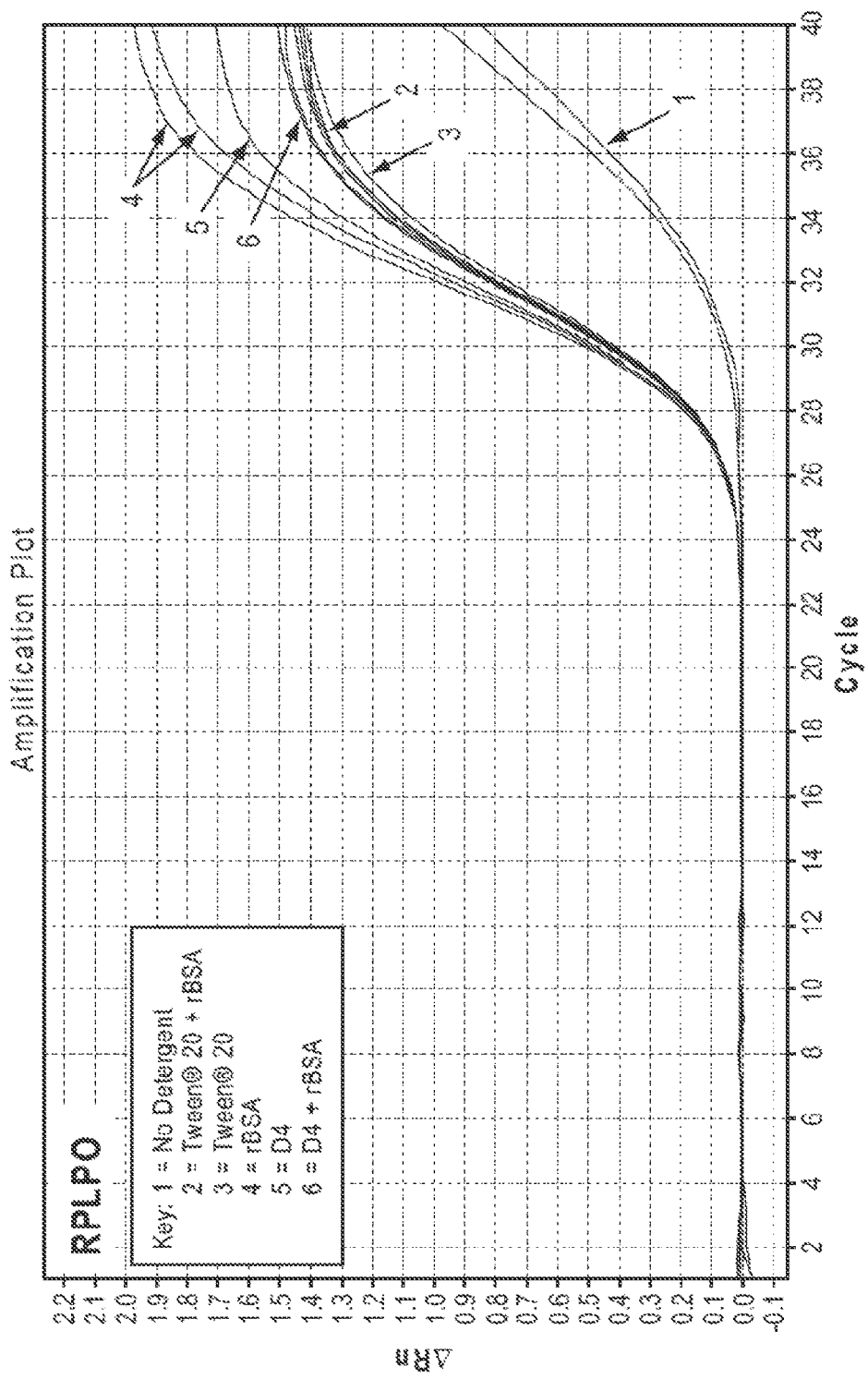
Figure 5J:
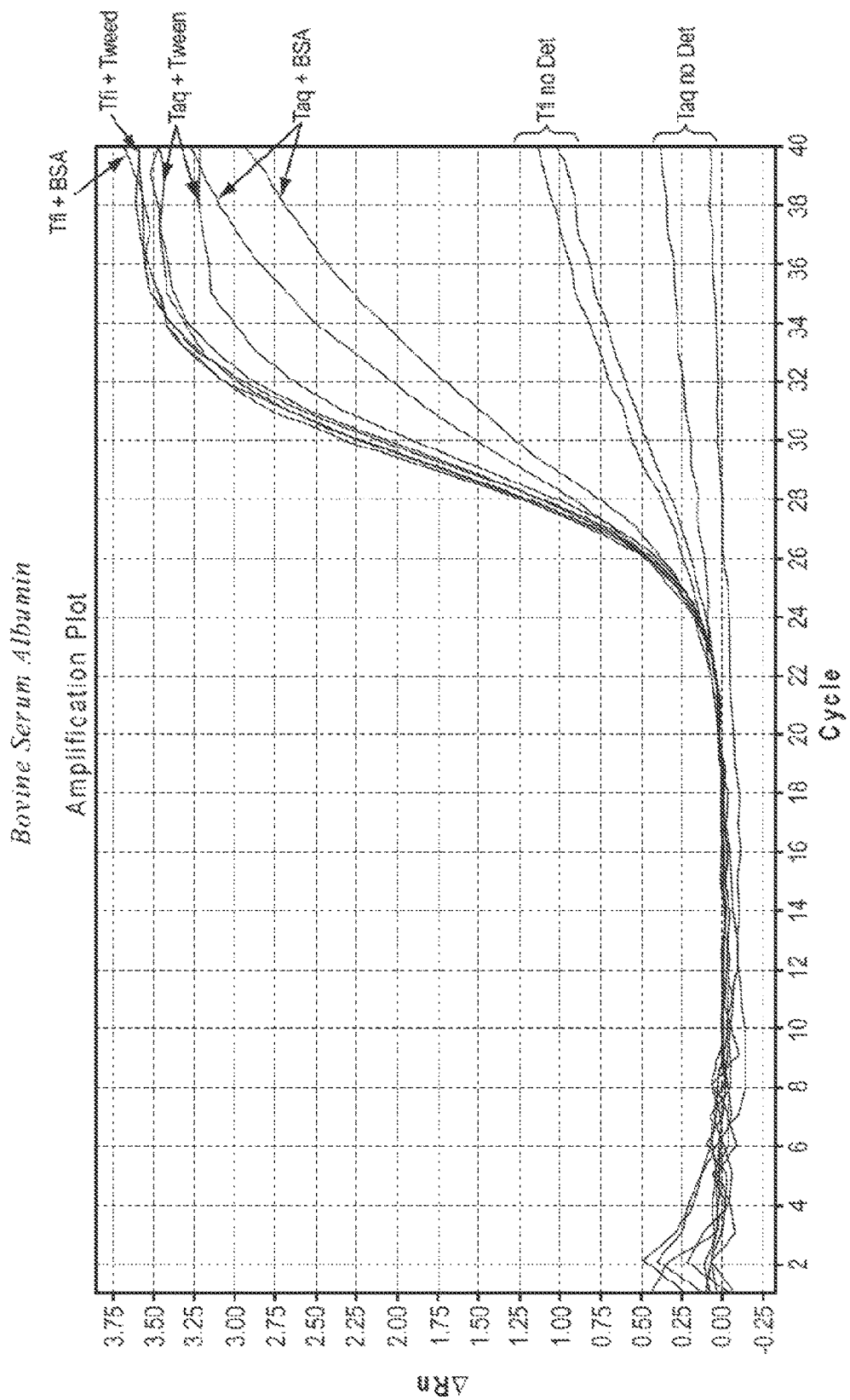
Figure 5K:
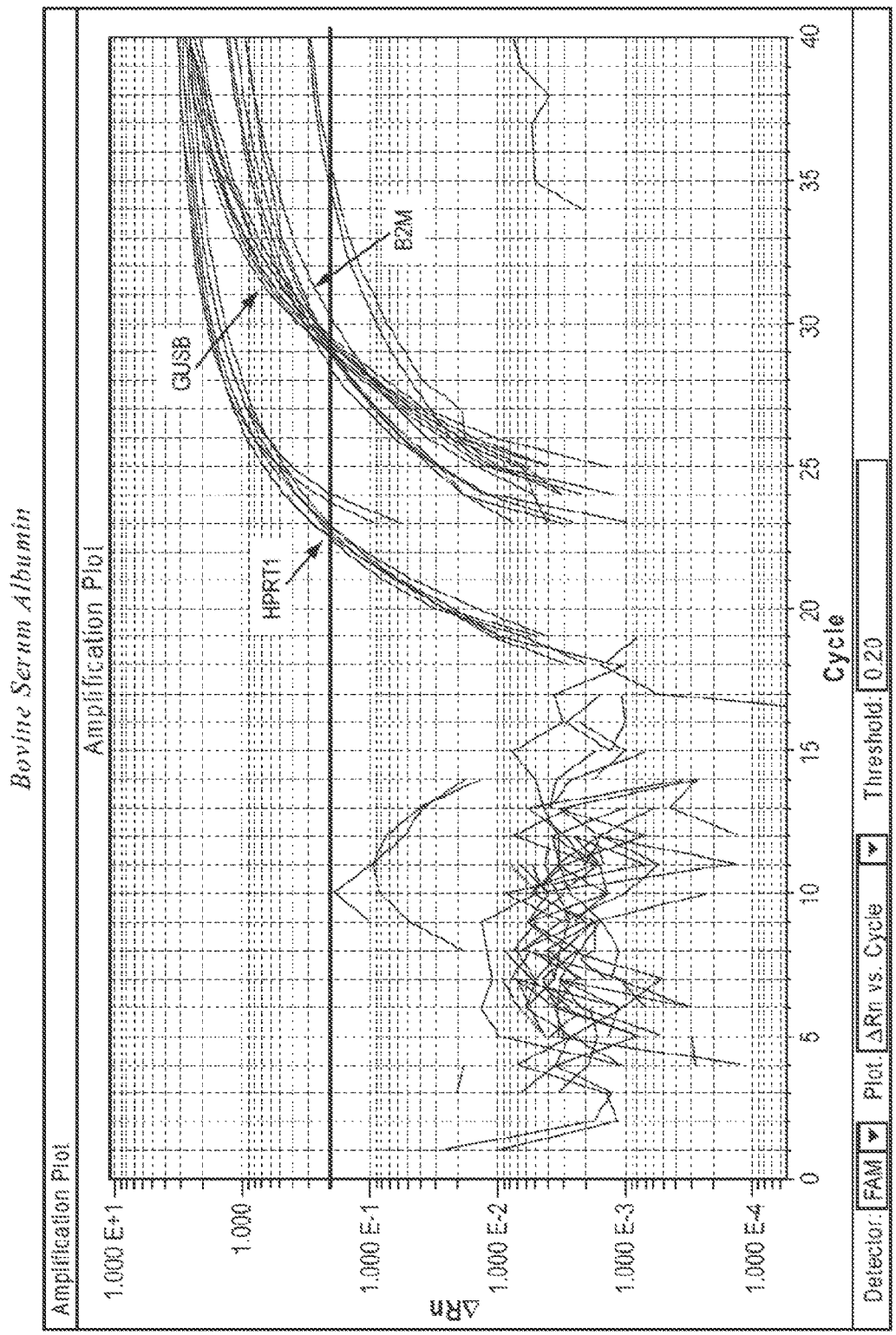
Figure 6:
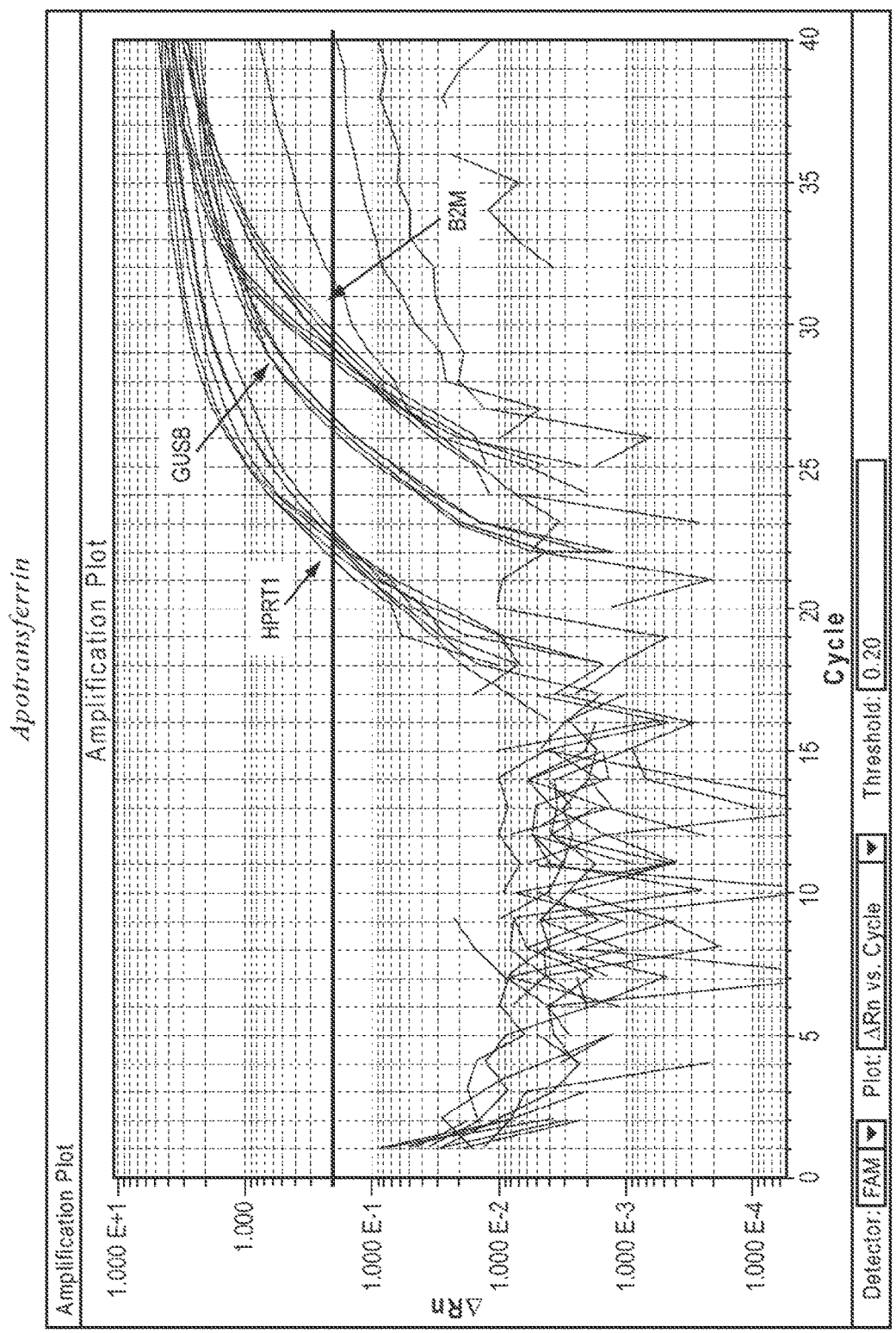
FIG. 6. An amplification plot of an amplification reaction using apotransferrin with HPRT1, GUSB or B2M as target nucleic acids according to certain exemplary embodiments of the methods and compositions disclosed herein.
Figure 7:
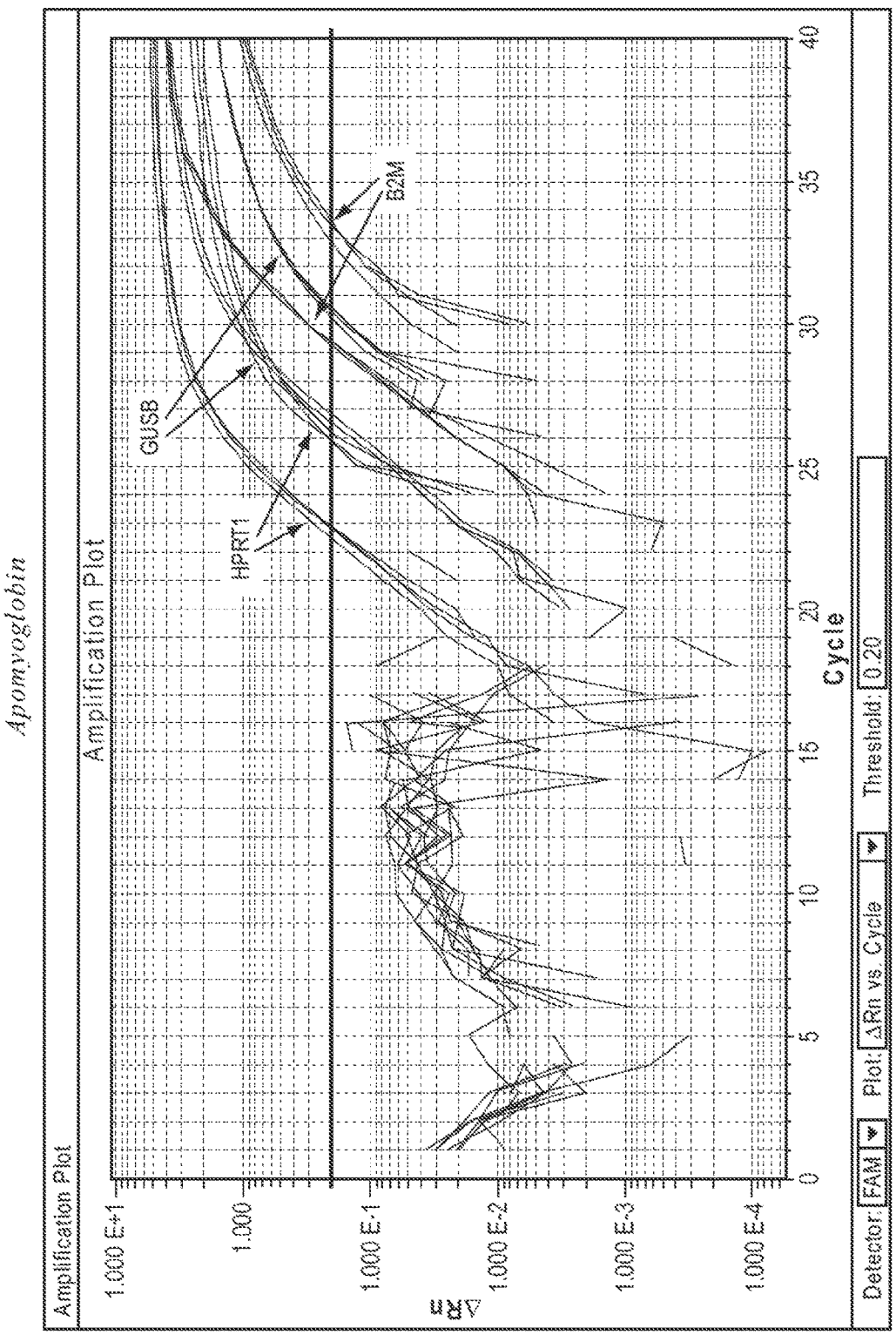
FIG. 7. An amplification plot of an amplification reaction using apomyoglobin with HPRT1, GUSB or B2M as target nucleic acids according to certain exemplary embodiments of the methods and compositions disclosed herein.
Figure 8:
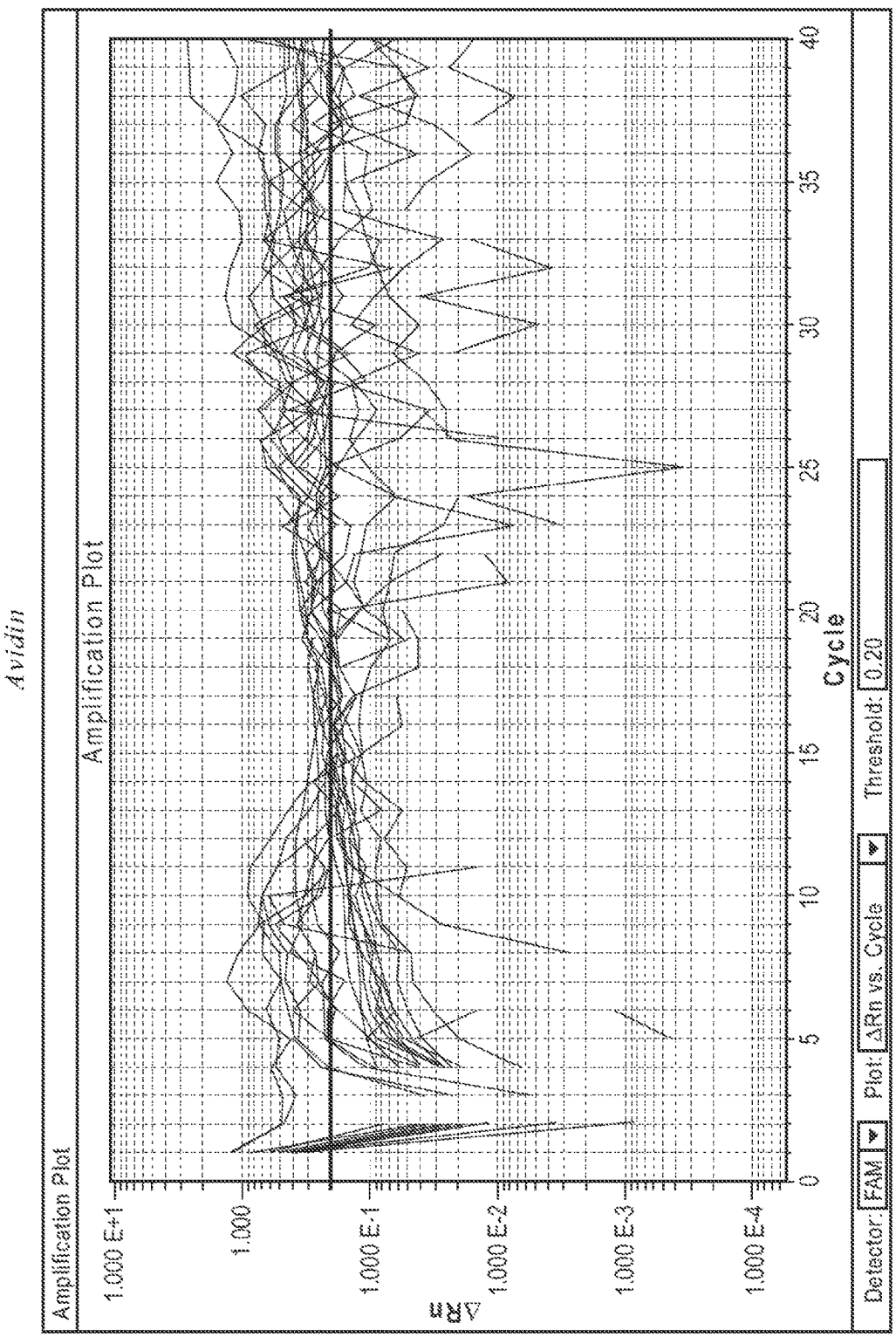
FIG. 8. An amplification plot of an amplification reaction using avidin according to certain exemplary embodiments of the methods and compositions disclosed herein.
Figure 9:
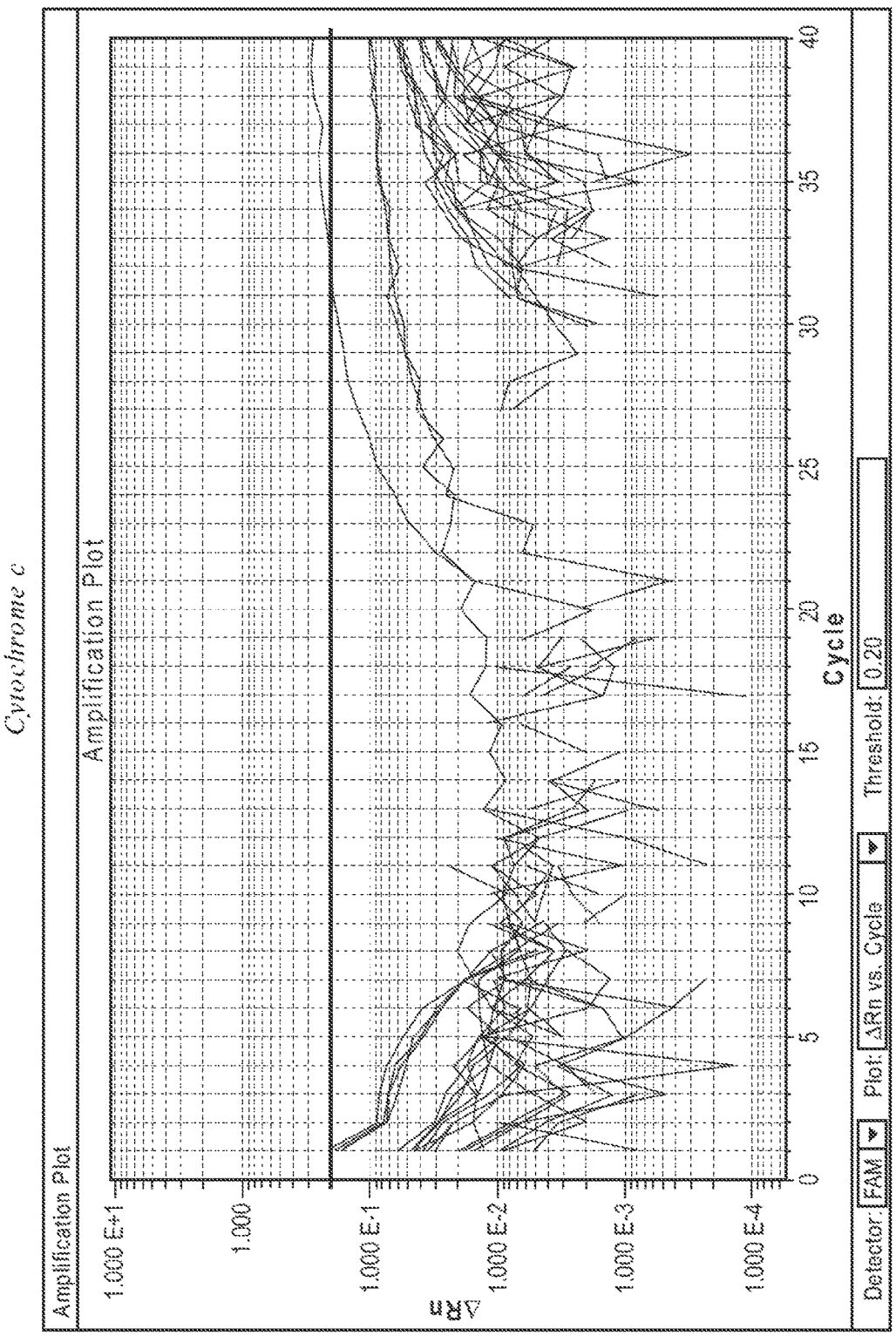
FIG. 9. An amplification plot of an amplification reaction using cytochrome C according to certain exemplary embodiments of the methods and compositions disclosed herein.
Figure 10A:
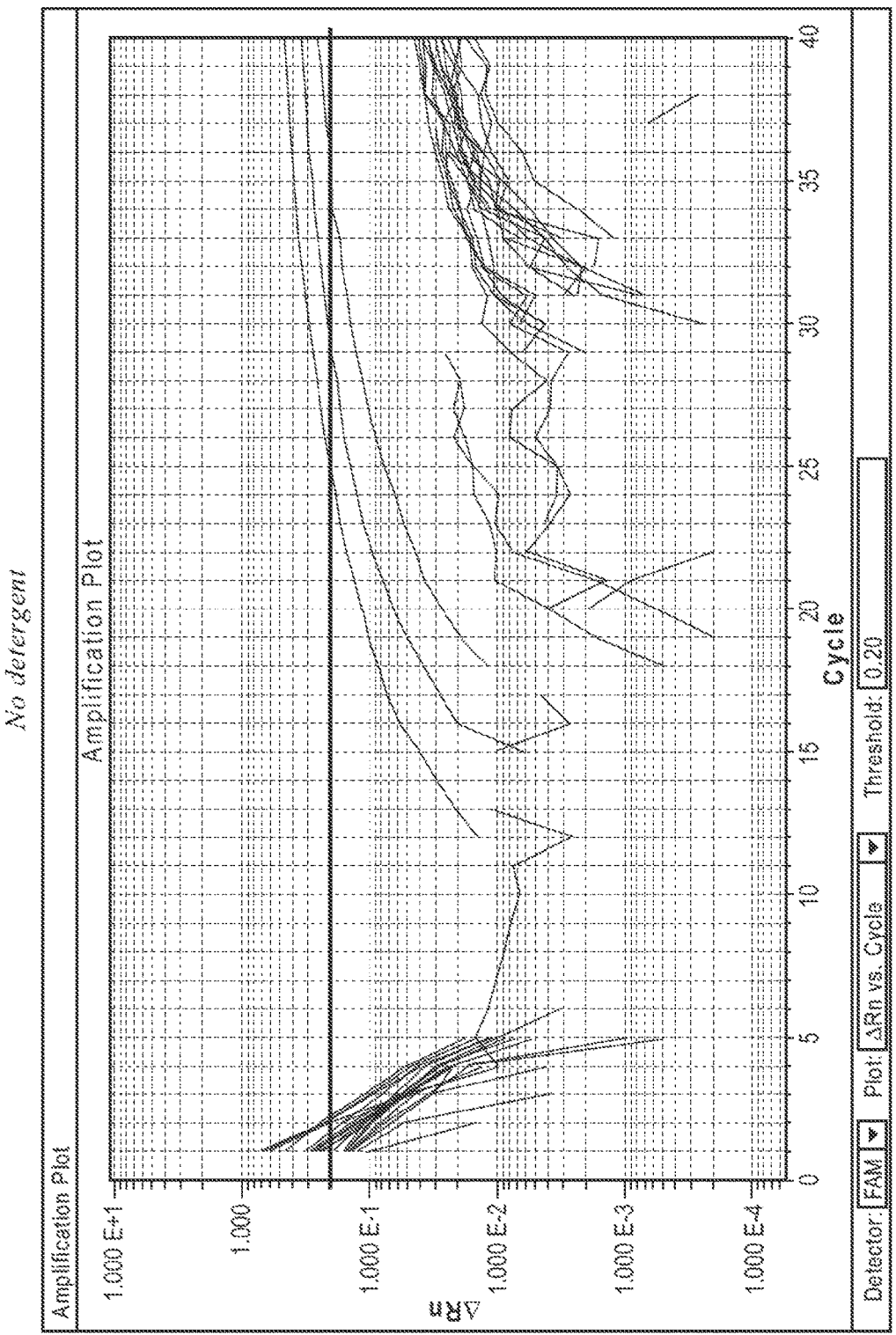
FIGS. 10A through 10B. Amplification plots of: A. Negative control amplification reaction (no detergent or protein having a low isoelectric point). B. Positive control amplification reaction of HPRT1, GUSB or B2M using Tween® 20.
Figure 10B:
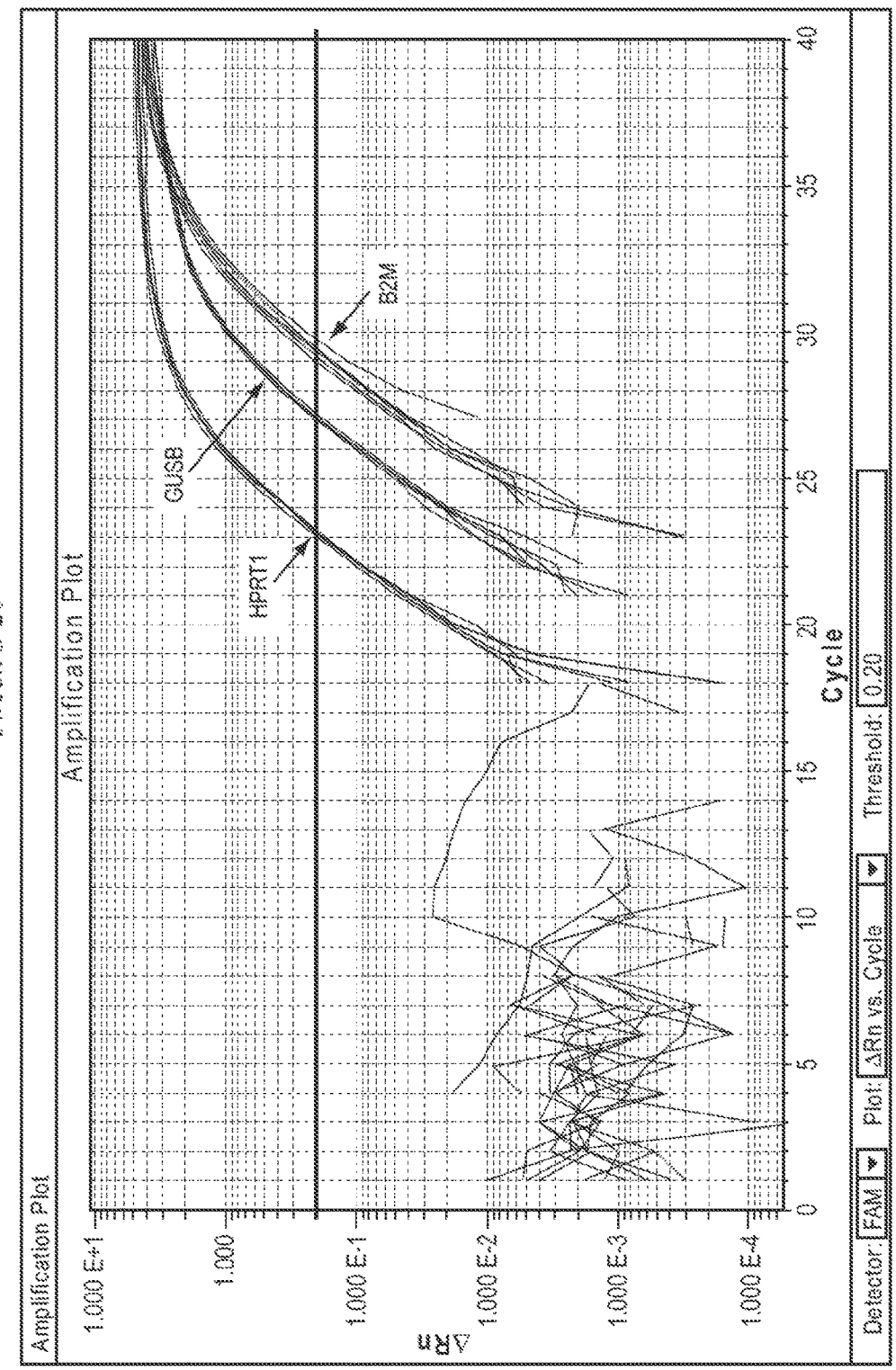

As shown in FIGS. 5A and 5B through 5E, 0.05 mg/ml BSA supports amplification of target nucleic acids by Taq polymerase in a manner comparable or better (e.g., GAPDH) than either 0.002% Dt4 ("D4") or 0.01% Tween® 20. It is noted that both natural bovine sourced BSA and recombinant BSA (expressed in *Pichia* yeast) were tested and the function of each is essentially identical. As shown in FIGS. 5B through 5E and 5F through 5I, the combination of Tween® 20 and BSA or Dt4 ("D4") and BSA also supports amplification of different target nucleic acids by Taq polymerase. FIGS. 5B through 5E also shows that BSA may better support amplification than either Tween® 20 or Dt4 ("D4") or a combination of BSA with either Tween® 20 or Dt4 ("D4"). FIG. 5J shows that BSA supports amplification of nucleic acid targets by the Tfi (e.g., LUX™ assay) and Taq DNA polymerases (e.g., LUX™ and TaqMan® assays).

Figure 11:
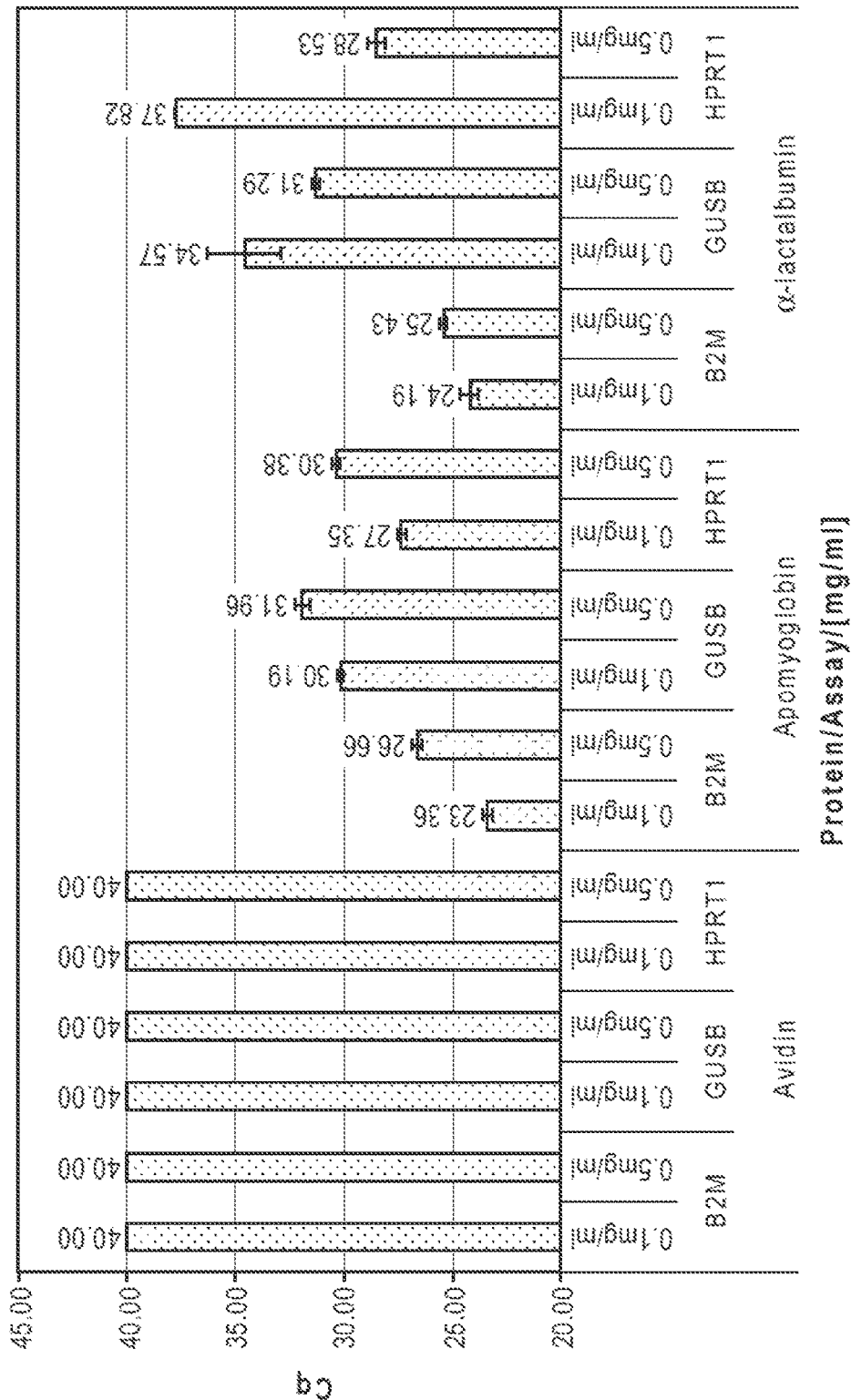
FIG. 11. A graphic representation of the use of avidin, apomyoglobin, or α-lactoalbumin in amplification reactions (Cq) according to certain exemplary embodiments of the methods and compositions disclosed herein.
Figure 12:
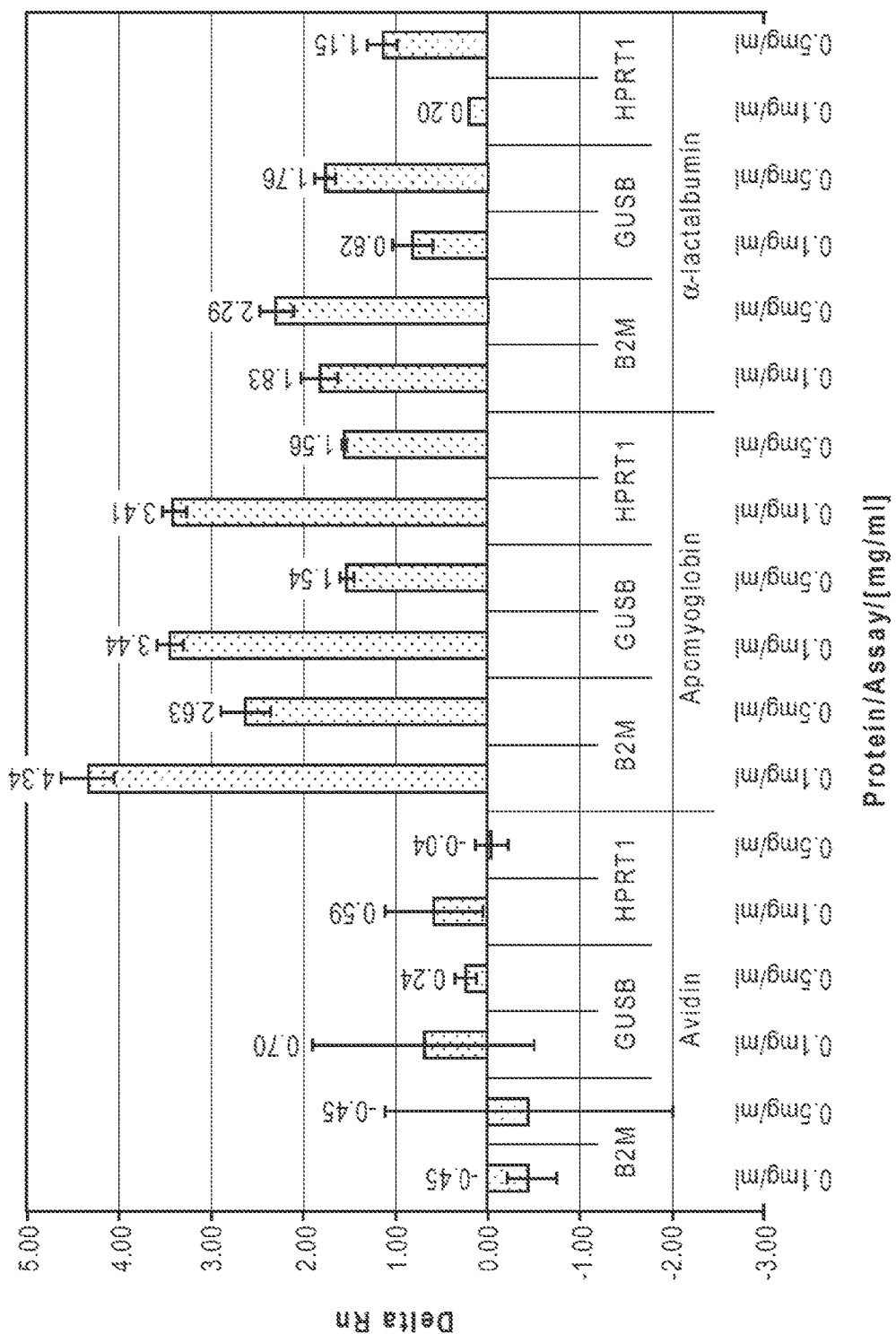
FIG. 12. A graphic representation of the use of avidin, apomyoglobin, or α-lactoalbumin in amplification reactions (Delta Rn) according to certain exemplary embodiments of the methods and compositions disclosed herein.
Figure 13:
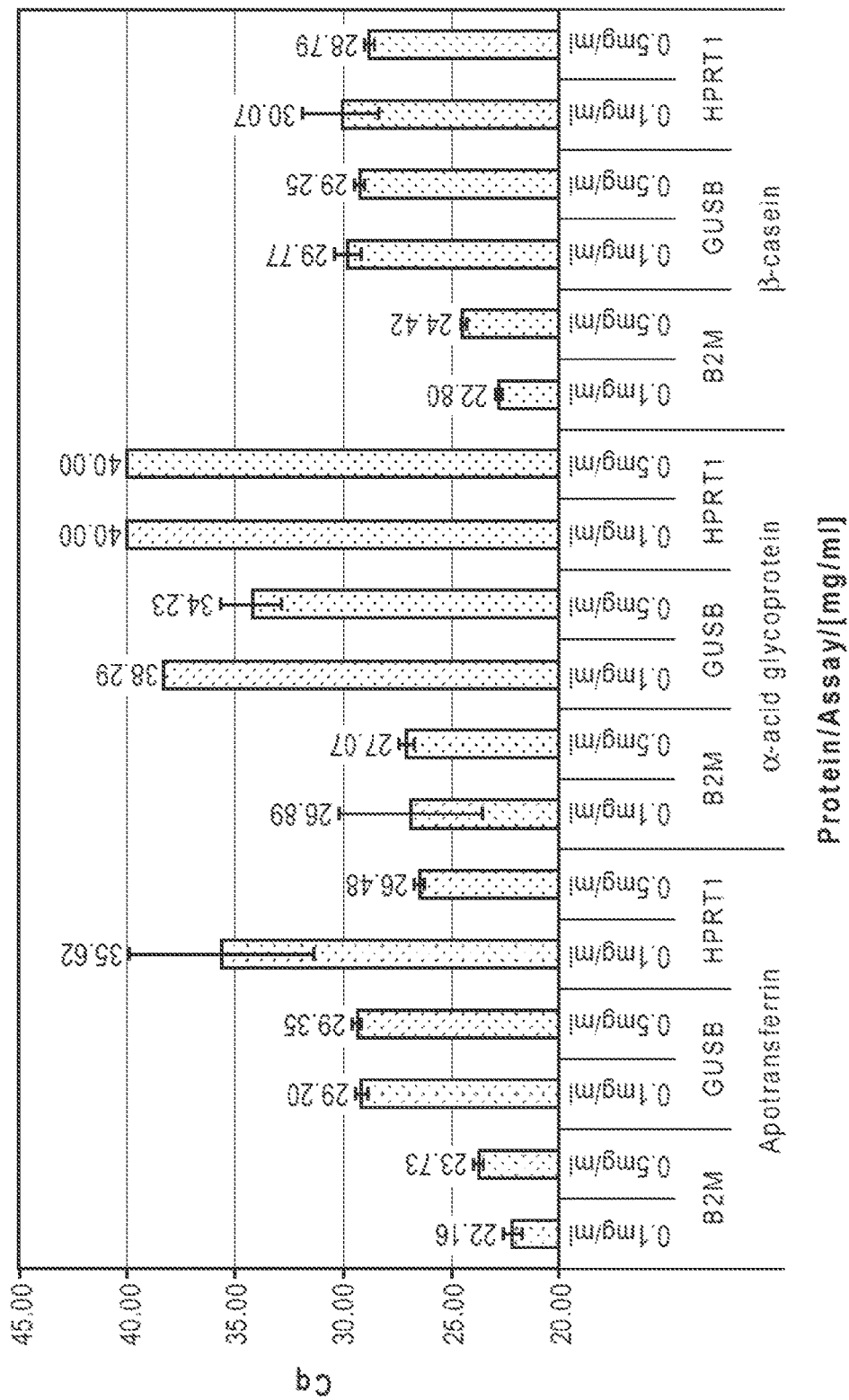
FIG. 13. A graphic representation of the use of apotransferrin, α-acid glycoprotein, or β-casein in amplification reactions (Cq) according to certain exemplary embodiments of the methods and compositions disclosed herein.
Figure 14:
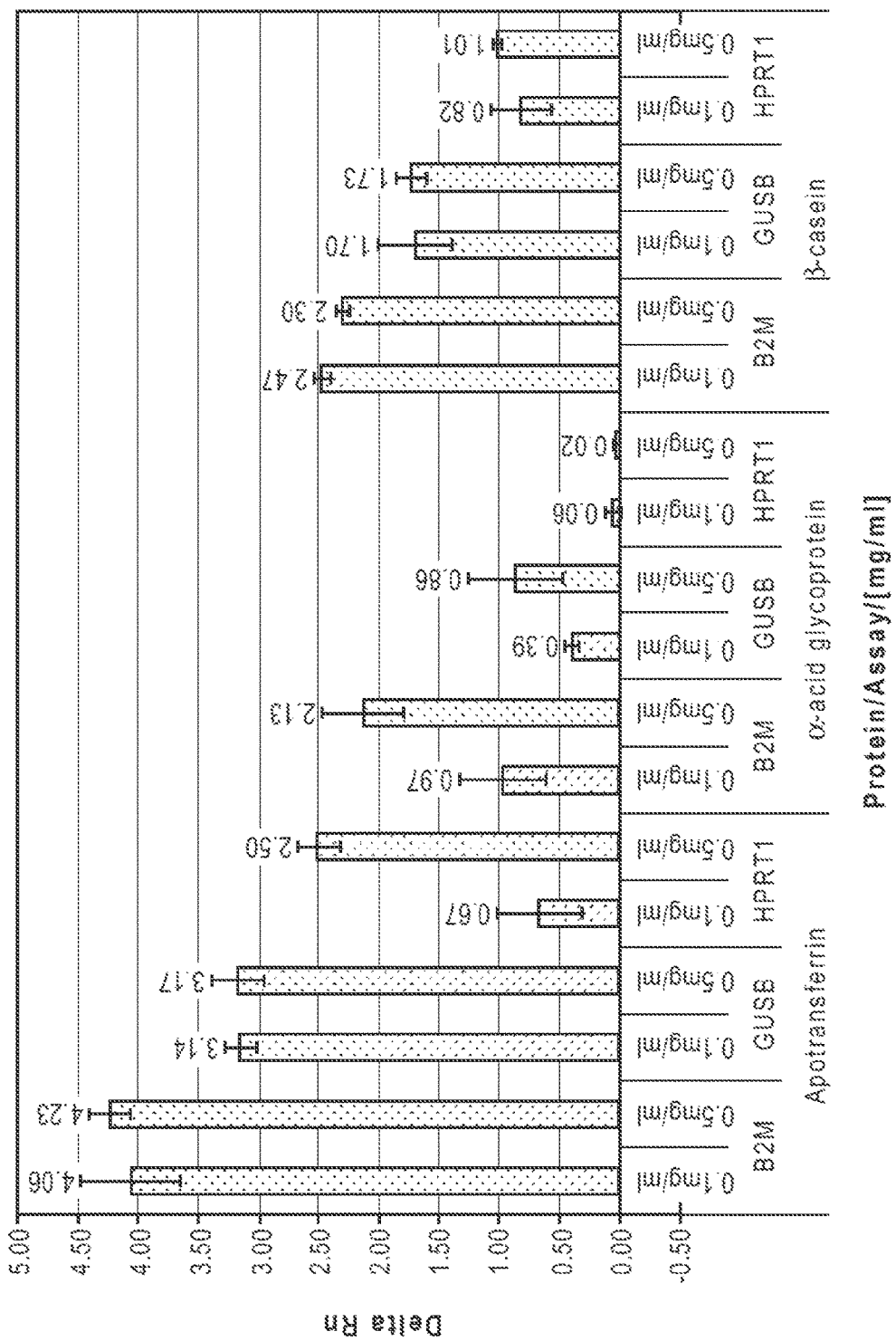
FIG. 14. A graphic representation of the use of apotransferrin, α-acid glycoprotein, or β-casein in amplification reactions (Delta Rn) according to certain exemplary embodiments of the methods and compositions disclosed herein.

FIGS. 11 (Cq) and 12 (delta Rn) demonstrate that apomyoglobin (iep 6.8-7.3) and α-lactalbumin (iep 4.2-4.5) support amplification of several target nucleic acids by Taq polymerase when included in the reaction mixture at either 0.1 mg/ml or 0.5 mg/ml. In this particular assay, Avidin (iep 10.5) did not support amplification. FIGS. 13 (Cq) and 14 (delta Rn) demonstrate that apotransferrin (iep 5.2-5.6) and α-acid glycoprotein (iep 3), and β-casein (iep 4.5) support amplification of several target nucleic acids by Taq polymerase when included in the reaction mixture at either 0.1 mg/ml or 0.5 mg/ml. FIG. 13 also shows that α-acid glycoprotein (iep 3), at least in this assay format, did not support amplification of target nucleic acid HPRT1, and provided less support for amplification of target nucleic acid GUSB than it did for B2M.

Figure 15:
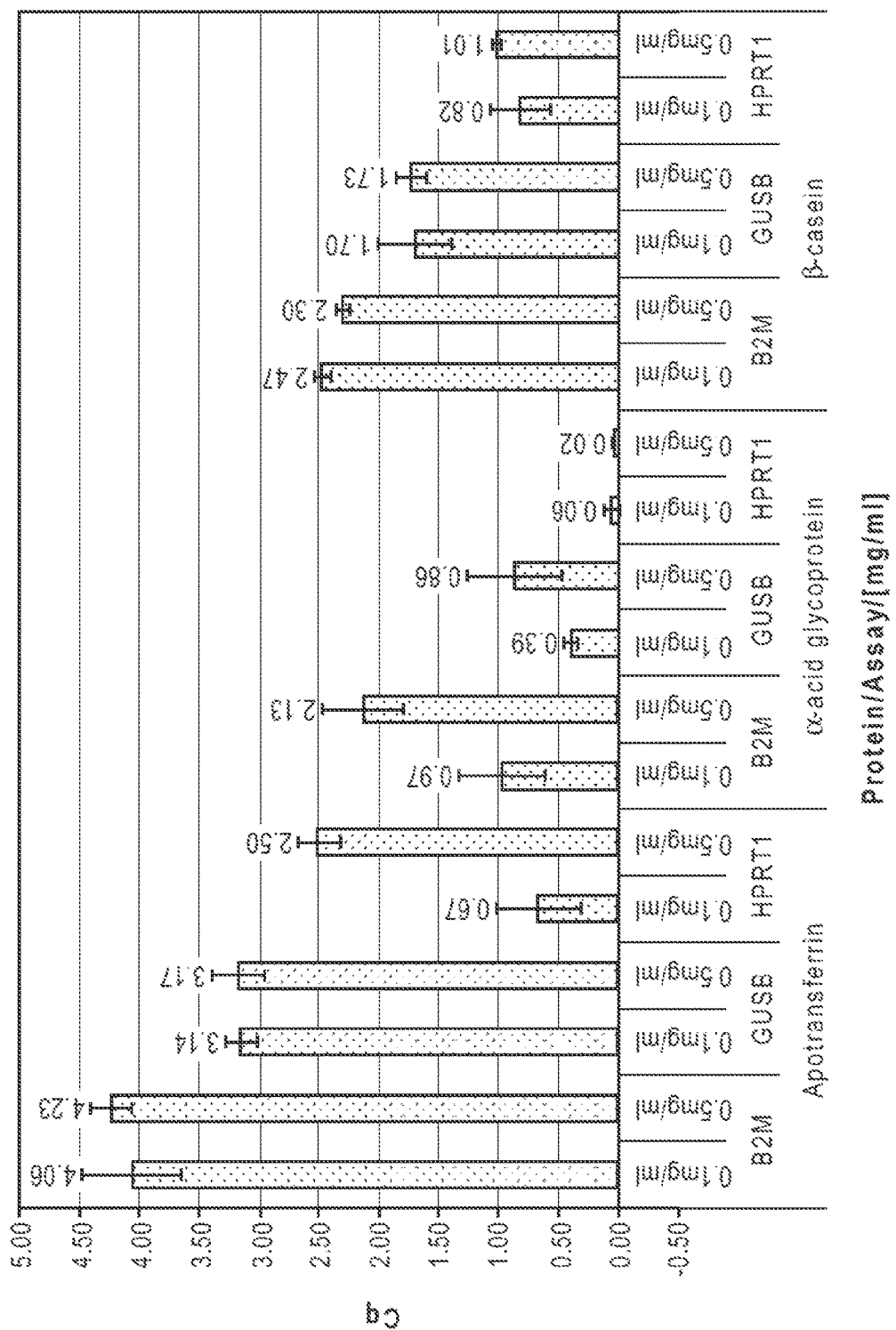
FIG. 15. A graphic representation of the use of cytochrome C, acetylated BSA, or BSA in amplification reactions (Cq) according to certain exemplary embodiments of the methods and compositions disclosed herein.
Figure 16:
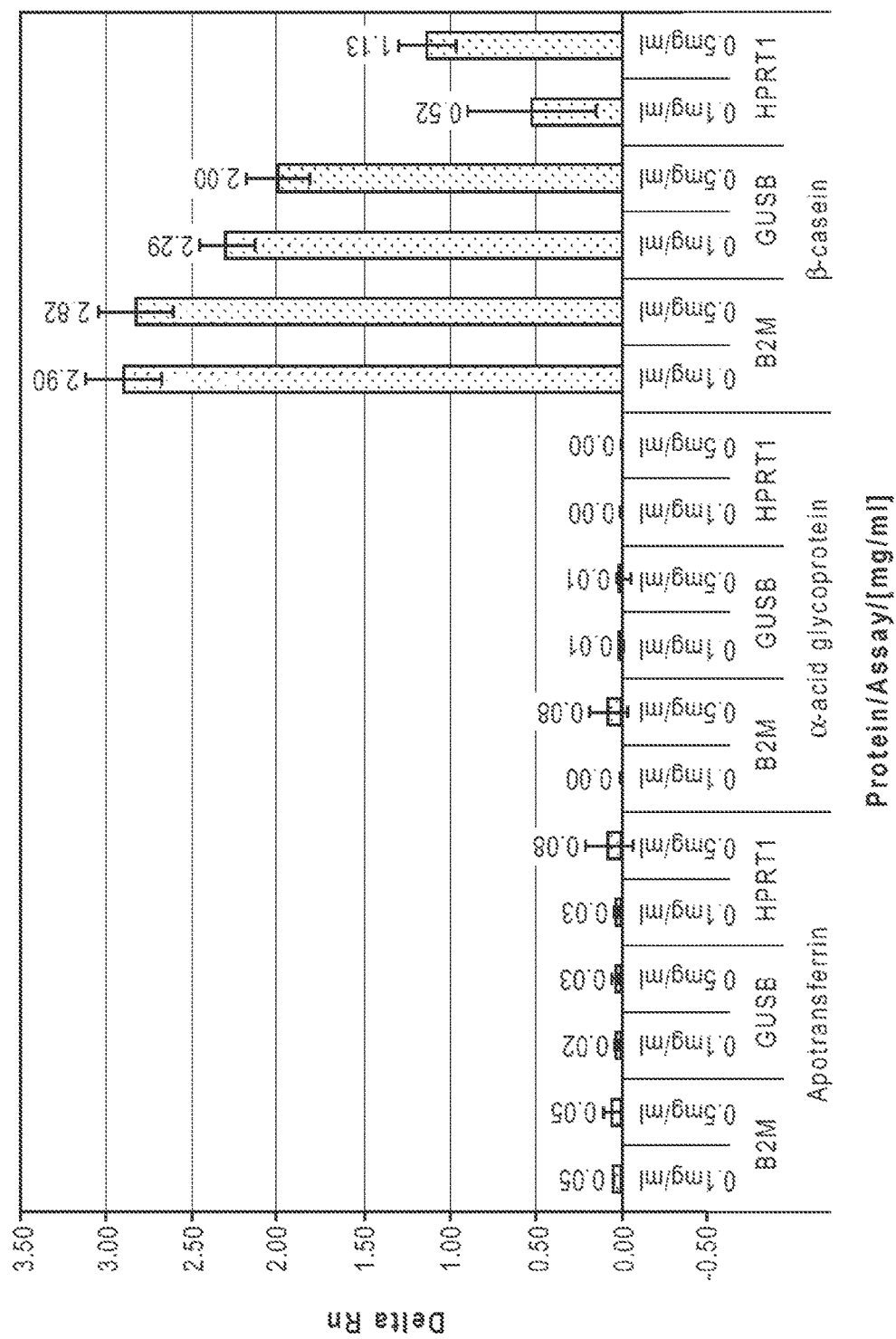
FIG. 16. A graphic representation of the use of cytochrome C, acetylated BSA, or BSA in amplification reactions (Delta Rn) according to certain exemplary embodiments of the methods and compositions disclosed herein.
Figure 17:
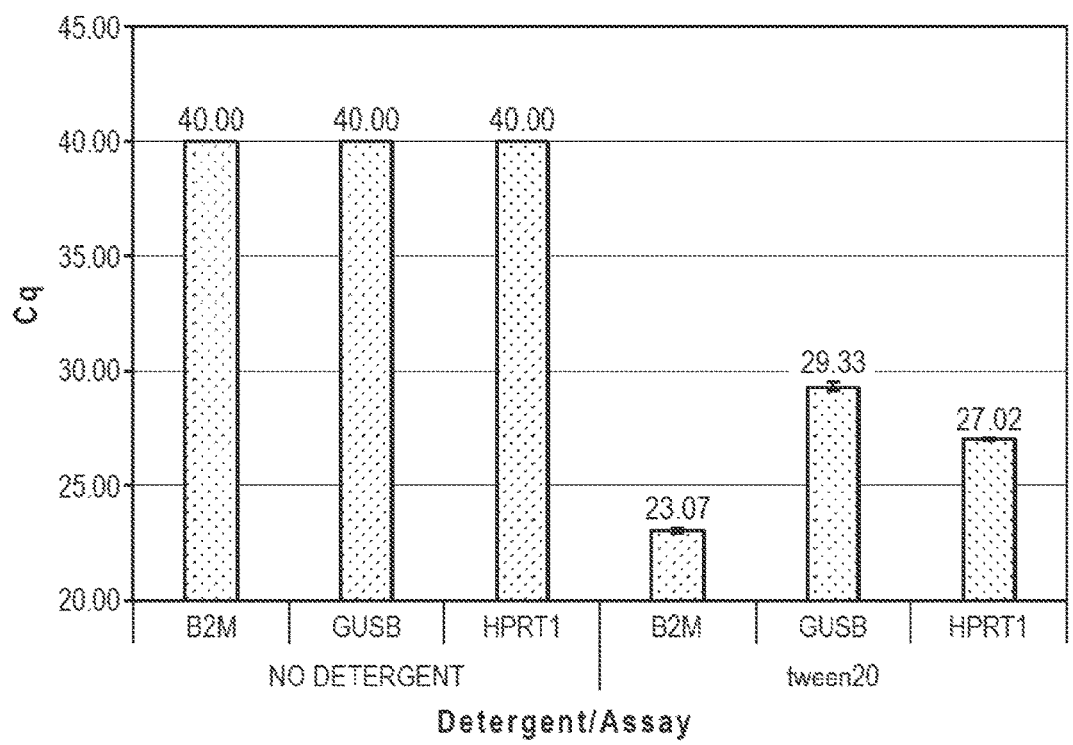
FIG. 17. A graphic representation of negative control (no detergent or protein having a low isoelectric point) and positive control (Tween® 20) amplification reactions (Cq) according to certain exemplary embodiments of the methods and compositions disclosed herein.
Figure 18:
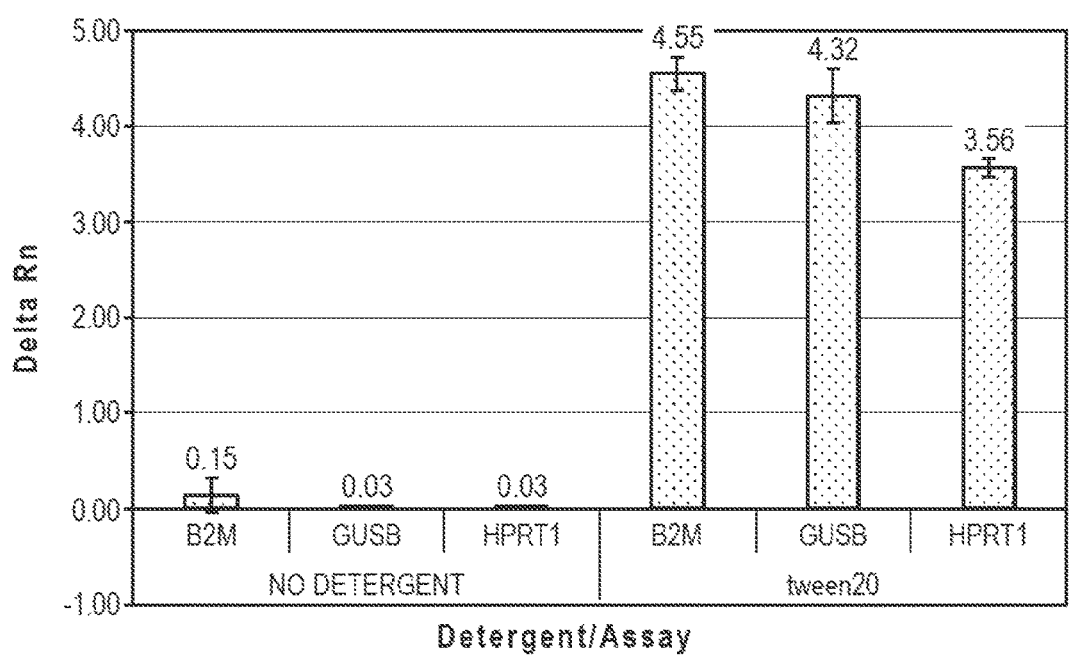
FIG. 18. A graphic representation of negative control (no detergent or protein having a low isoelectric point) and positive control (Tween® 20) amplification reactions (Delta Rn) according to certain exemplary embodiments of the methods and compositions disclosed herein.

FIGS. 15 (Cq) and 16 (delta Rn) confirm that recombinant BSA (iep 4.7) supports amplification of several target nucleic acids by Taq polymerase when included in the reaction mixture at either 0.1 mg/ml or 0.5 mg/ml. Neither cytochrome c (iep 10-10.5) nor acetylated BSA (iep<4) supported amplification of the target nucleic acids tested.

All references cited within this disclosure are hereby incorporated by reference in their entirety. While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A method for detecting a target nucleic acid in a sample, said method comprising:
   a) forming a reaction mixture comprising at least one polymerase, a first primer, dNTPs, at least one protein having a low isoelectric point, and a second primer or a probe comprising a detectable label, wherein said reaction mixture is substantially free of a detergent;
   b) amplifying said target nucleic acid; and,
   c) detecting a signal generated from said detectable label indicative of the presence and/or amount of said target nucleic acid.

2. The method of claim 1, wherein said polymerase is thermostable.

3. The method of claim 1, wherein said at least one protein having a low isoelectric point is bovine serum albumin (BSA).

4. The method of claim 1, wherein said at least one protein having a low isoelectric point is selected from the group consisting of β-lactoglobulin, apomyoglobin, α-lactoalbumin, apotransferrin, α-acid glycoprotein, and β-casein.

5. The method of claim 1, wherein said at least one protein having a low isoelectric point is a negatively charged, globular protein when present in said reaction mixture.

6. The method of claim 1, wherein said at least one protein having a low isoelectric point has an isoelectric point less than 8 when present in said reaction mixture.

7. The method of claim 1, wherein said isoelectric point is between about 4 and about 7.

8. The method of claim 1, wherein said isoelectric point is between about 4.2 to about 5.3.

9. The method of claim 1, wherein said target nucleic acid is further quantitated.

10. The method of claim 1, wherein said thermostable polymerase is selected from the group consisting of Taq DNA polymerase, Tfi DNA polymerase, Tfl DNA polymerase, Pfu DNA polymerase, and Vent™ DNA polymerase, a polymerase having reduced 3' to 5' exonuclease activity, SuperScript™ DNA polymerase, a genetically engineered DNA polymerase, a polymerase having the active site mutation F667Y, a polymerase having the equivalent of active site F667Y, Tth polymerase, and a derivative or a fragment thereof.

11. The method of claim 1, wherein said thermostable polymerase is Taq DNA polymerase.

12. The method of claim 1, wherein said thermostable polymerase is Tfi DNA polymerase.

13. The method of claim 1, wherein said protein having a low isoelectric point is globular.

14. The method of claim 1, wherein said protein having a low isoelectric point comprises no modifying groups.

* * * * *